United States Patent
He et al.

(10) Patent No.: US 12,428,666 B2
(45) Date of Patent: *Sep. 30, 2025

(54) COMPOSITIONS AND METHODS RELATED TO KETHOXAL DERIVATIVES

(71) Applicant: The University of Chicago, Chicago, IL (US)

(72) Inventors: Chuan He, Chicago, IL (US); Xiaocheng Weng, Chicago, IL (US); Tong Wu, Chicago, IL (US)

(73) Assignee: THE UNIVERSITY OF CHICAGO, Chicago, IL (US)

( * ) Notice: Subject to any disclaimer, the term of this patent is extended or adjusted under 35 U.S.C. 154(b) by 1174 days.

This patent is subject to a terminal disclaimer.

(21) Appl. No.: 17/250,023

(22) PCT Filed: May 8, 2019

(86) PCT No.: PCT/US2019/031287
§ 371 (c)(1),
(2) Date: Nov. 6, 2020

(87) PCT Pub. No.: WO2019/217533
PCT Pub. Date: Nov. 14, 2019

(65) Prior Publication Data
US 2021/0214773 A1    Jul. 15, 2021

Related U.S. Application Data

(60) Provisional application No. 62/668,543, filed on May 8, 2018, provisional application No. 62/668,994, filed on May 9, 2018.

(51) Int. Cl.
C07C 69/003    (2006.01)
C12N 15/11    (2006.01)
C12Q 1/6806    (2018.01)

(52) U.S. Cl.
CPC .......... *C12Q 1/6806* (2013.01); *C07C 69/003* (2013.01); *C12N 15/11* (2013.01); *C12N 2830/46* (2013.01); *C12Q 2565/518* (2013.01)

(58) Field of Classification Search
None
See application file for complete search history.

(56) References Cited

U.S. PATENT DOCUMENTS 2,889,243 A    6/1959    Underwood et al.
5,385,933 A    1/1995    Rabinovitz et al.
7,133,783 B2   11/2006   Noller et al.

FOREIGN PATENT DOCUMENTS

CN    112384524 A    2/2021
JP    H02-150299    6/1990
WO    WO 2019/217549 A1    11/2019

OTHER PUBLICATIONS

Aw et al, "In Vivo Mapping of Eukaryotic RNA Interactomes Reveals Principles of Higher-Order Organiation and Regulation", Mol Cell., 62(4):603-617, 2016.

(Continued)

*Primary Examiner* — Adam C Milligan
*Assistant Examiner* — Jason M. Nolan
(74) *Attorney, Agent, or Firm* — NORTON ROSE FULBRIGHT US LLP

(57) ABSTRACT

Embodiments are directed to $N_3$-kethoxal reagents and derivatives thereof, and related methods that allow fast and reversible labeling of single-stranded nucleic acids in live cells. By way of example, one aspect is directed to a process for reversible labeling of single-stranded guanine bases in live cells, which results in an effective in vivo method for transcriptome-wide RNA secondary structure mapping and RNA G-quadruplex prediction.

15 Claims, 19 Drawing Sheets

(56) References Cited

OTHER PUBLICATIONS

Buenrostro et al., "Transposition of native chromatin for fast and sensitive epigenomic profiling of open chromatin, DNA-binding proteins and nucleosome position", Nat Methods., 10(12):1213-1218, 2013.
Core et al., "Nascent RNA sequencing reveals widespread pausing and divergent initiation at human promoters", 322(5909):1845-1848, 2008.
Ding et al., "In vivo genome-wide profiling of RNA secondary structure reveals novel regulatory features", Nature., 505(7485):696-700, 2014.
Esfand and Tomalia, "Poly(amidoamine) (PAMAM) dendrimers: from biomimicry to drug delivery and biomedical applications", Drug Discov Today., 6(8):427-436, 2001.
Feng et al., "Light-activated chemical probing of nucleobase solvent accessibility inside cells", Nat Chem Biol., 14(3):276-283, 2018.
Jiang et al., "Enantioselective synthesis for the antipodes of slagenins B and C: establishment of absolute stereochemistry", Org Lett., 3(25):4011-4013, 2001.
Kertesz et al., "Genome-wide measurement of RNA secondary structure in yeast", Nature, 467(7311):103-107, 2010.
Kubota et al., "Progress and challenges for chemical probing of RNA structure inside living cells", Nat Chem Biol., 11(12):933-941, 2015.
Lee et al., "Comparison of SHAPE reagents for mapping RNA structures inside living cells", RNA, 23:169-174, 2017.
Lewis et al., "RNA modifications and structures cooperate to guide RNA-protein interactions", Nat Rev Mol Cell Biol., 18(3):202-210, 2017.
Lo et al., "Synthesis, radiochemical characterization and biodistribution of Tc-99m labeled kethoxal bis(thiosemicarbazone) complexes", Journal of Labelled Compounds and Radiopharmaceuticals, 44:S654-S656, 2001.
Lu and Chang, "Decoding the RNA structurome", Curr Opin Struct Biol., 36:142-148, 2016.
Lu et al., "RNA Duplex Map in Living Cells Reveals Higher-Order Transcriptome Structure", Cell., 165(5):1267-1279, 2016.
Lucks et al., "Multiplexed RNA structure characterization with selective 2'-hydroxyl acylation analyzed by primer extension sequencing (SHAPE-Seq)", Proc Natl. Acad Sci USA., 108(27):11063-11068, 2011.
Nainar et al., "Temporal Labeling of Nascent RNA Using Photoclick Chemistry in Live Cells", J Am Chem Soc., 139(24):8090-8093, 2017.
Pubmed Compound Summary for CID 109466, Butanal, 3-(heptyloxy)-2-oxo-, U.S. National Library Medicine, Aug. 8, 2005 (Aug. 8, 2005), p. 1-10; p. 2 (https://pubchem.ncbi.nlm.nih.gov/compound/109466).
Pubmed Compound Summary for CID 134685, "Bikethoxal", U.S. National Library of Medicine, Aug. 8, 2005 (Aug. 8, 2005), p. 1-10; p. 2 (https://pubchem.ncbi.nlm.nih.gov/compound/134685).
Pubmed Compound Summary for CID 226599, '3-[2-(Methoxymethoxy)ethoxy]-2-oxobutanal', U.S. National Library of Medicine, Mar. 26, 2005 (Mar. 26, 2005), p. 1-8; p. 2 (https://pubchem.ncbi.nlm.nih.gov/compound/226599).
Ramani et al., "High-throughput determination of RNA structure by proxmity ligation", Nat Biotechnol., 33(9):980-984, 2015.
Rouskin et al., "Genome-wide probing of RNA structure reveals active unfolding of mRNA structures in vivo", Nature., 505(7485):701-705, 2014.
Sharma et al, "Global Mapping of Human RNA-RNA Interactions", Mol Cell., 62(4):618-626, 2016.
Siegfried et al., "RNA motif discovery by SHAPE and mutational profiling (SHAPE-MaP)", Nat. Methods, 11(9):959-965, 2014.
Spitale et al., "Structural imprints in vivo decode RNA regulatory mechanisms", Nature., 519(7544):486-490, 2015.
Strobel et al., "High-throughput determination of RNA structures", Nat Rev Genet., 19(10):615-634, 2018.
Talkish et al, "Mod-seq: high-throughput sequencing for chemical probing of RNA structure", RNA, 20(5):713-720, 2014.
Underwood et al., "FragSeq: transcriptome-wide RNA structure probing using high-througput sequencing", Nat Methods., 7(12):995-1001, 2010.
Wan et al., "Landscape and variation of RNA secondary structure across the human transcriptome", Nature., 505(7485):706-709, 2014.
Xu and Culver, "Chemical probing of RNA and RNA/protein complexes", Methods Enzymol., 468:147-165, 2009.
Zubradt et al., "DMS-MaPseq for genome-wide or targeted RNA structure probing in vivo", Nat. Methods., 14(1):75-82, 2017.
Shapiro, et al: "On the Reaction of Guanine with Glyoxal, Pyruvaldehyde, and Kethoxal, and the Structure of the Acylguanines. A New Synthesis of $N^2$-Alkylguanines", Biochem., 8(1), (1969), pp. 238-245.
"3-Azido-2-oxopropanal" Pubchem CID 54201527 deposited on Dec. 4, 2011, pp. 1-8, https://pubchem.ncbi.nlm.nih.gov/compound/3-Azido-2-oxopropanal. Accessed Sep. 20, 2024.
Bocchetta et al., "23S rRNA Positions Essential for tRNA binding in Ribosomal Functional Sites," Proc. Natl. Acad. Sci. USA, 1998, vol. 95, pp. 3525-3530.
Booth and Sartorelli, "Synergistic Interaction of Kethoxal bis(Thiosemicarbazone) and Cupric Ions in Sarcoma 180," Nature 1966, 210, 104-105.
Brewer et al., "Ribonucleic acid-protein crosslinking within the intact *Escherichia coli* ribosome, utilizing ethylene glycol bis[3-(2-ketobutyraldehyde) ether], a reversible, bifunctional reagent: synthesis and crosslinking within 30S and 50S subunits," Biochemistry 1983, 22(18), 4303-4309.
Christian et al., "Analysis of substrate recognition by the ribonucleoprotein endonuclease RNase P," Methods, 2002, vol. 28, pp. 307-322.
International Search Report and Written Opinion issued in PCT Application No. PCT/US2020/070073, dated Sep. 14, 2020, 10 pages.
Noller et al., "Functional Modification of 16S Ribosomal RNA by Kethoxal," Proc. Natl. Acad. Sci. USA, 1972, vol. 69(11 ), pp. 3115-3118.
Staehelin, M. "Inactivation of virus nucleic acid with glyoxal derivatives," Biochimca Biophysica Acta 1959, 31 :448-54.
Tiffany et al., "Antiviral Compounds. I. Aliphatic Glyoxals, a-Hydroxyaldehydes and Related Compounds," J. Am. Chem. Soc. 1957, 79(7), 1682-1687.

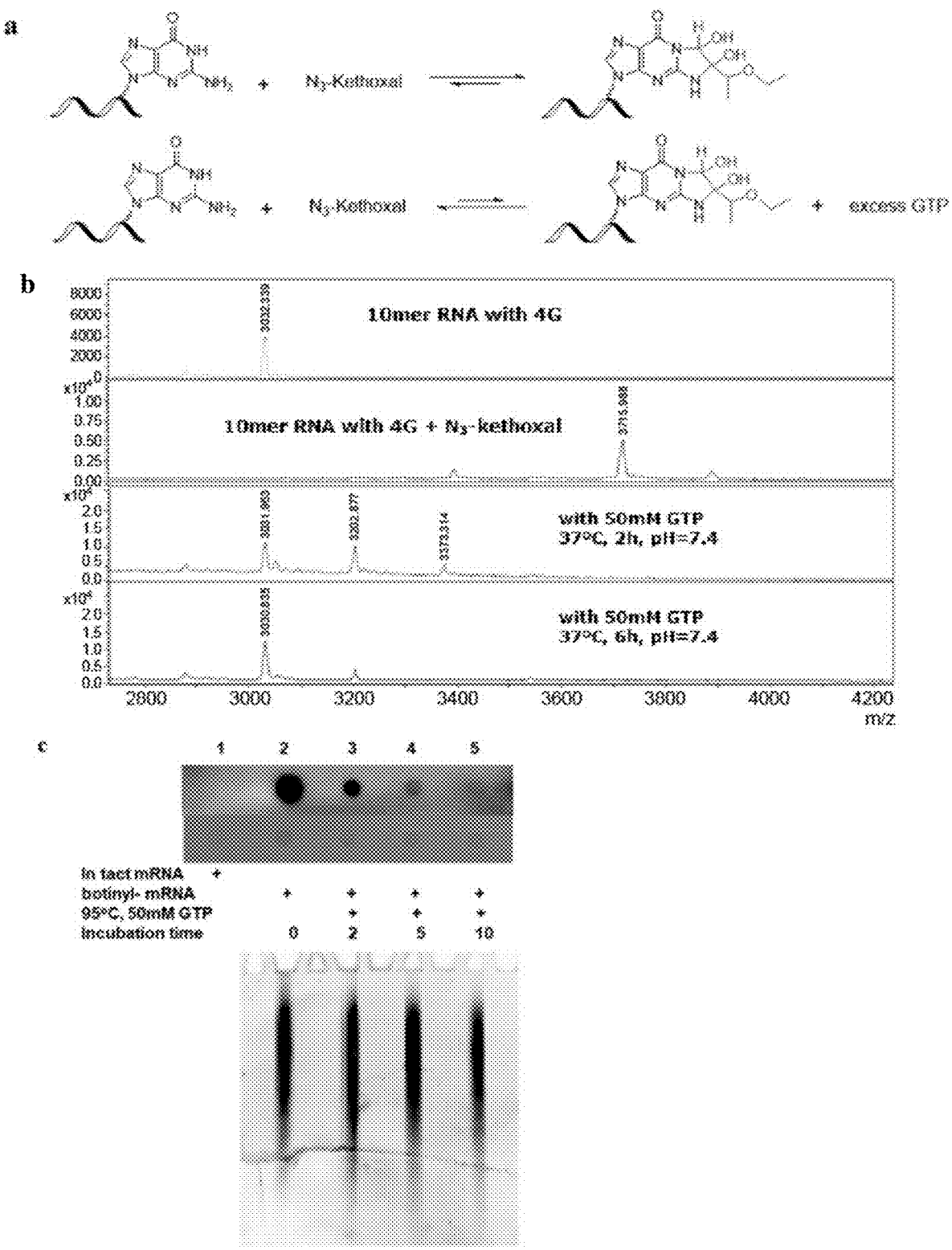
FIG. 12A-C

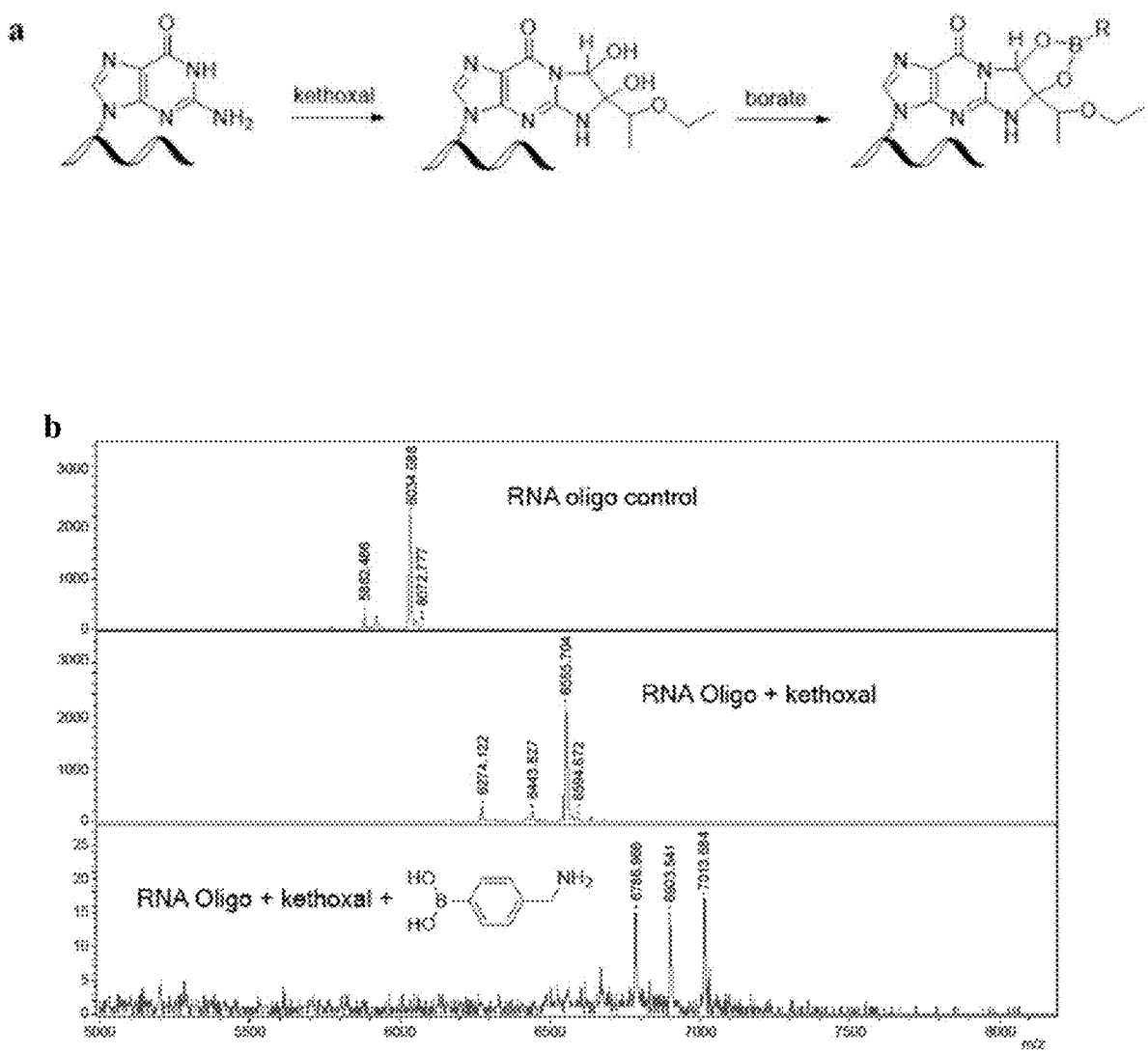
FIG. 13A-B

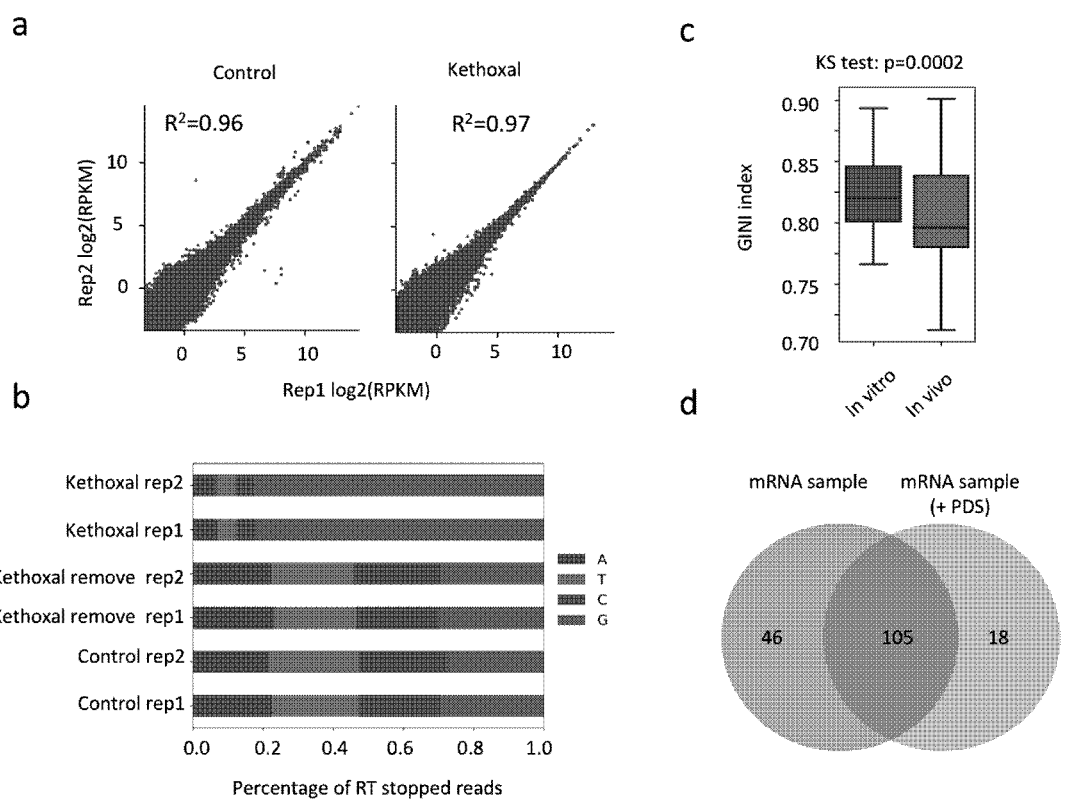
FIG. 14A-D

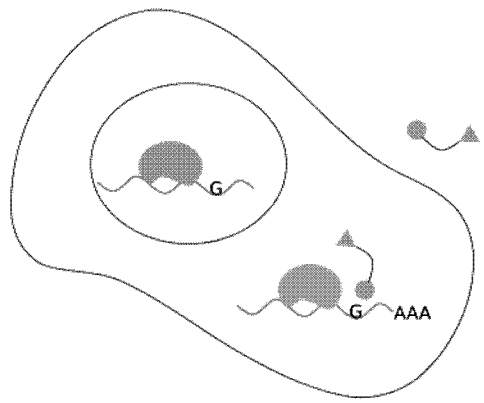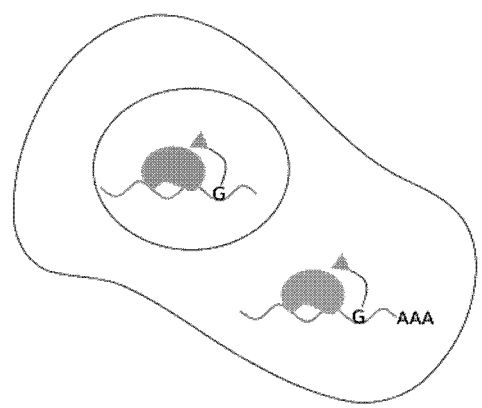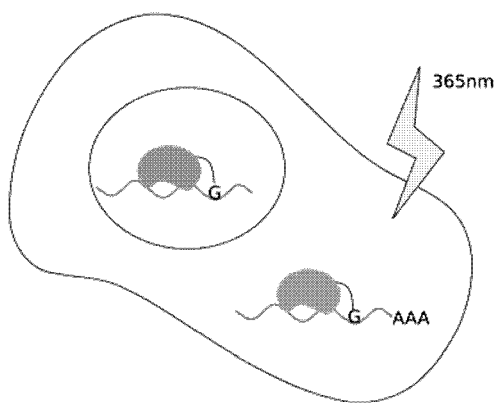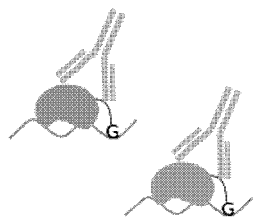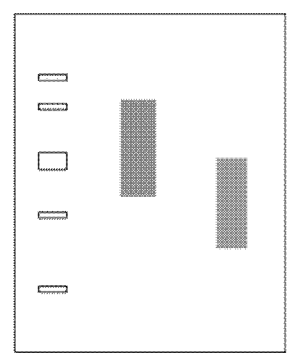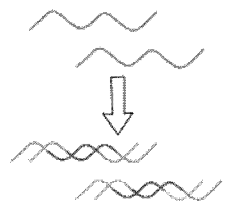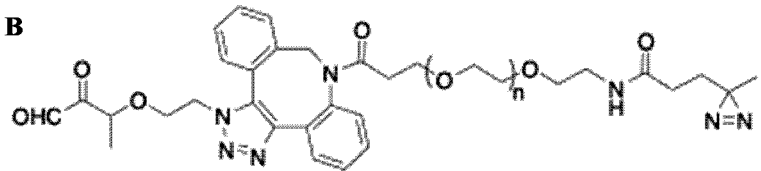
FIG. 18A-B

COMPOSITIONS AND METHODS RELATED TO KETHOXAL DERIVATIVES

CROSS REFERENCE TO RELATED APPLICATIONS

This application is a national phase application under 35 U.S.C. § 371 of International Application No. PCT/US2019/031287 filed May 8, 2019, which claims the benefit of priority to U.S. Provisional Patent Application No. 62/668,543 filed May 8, 2018 and U.S. Provisional Patent Application No. 62/668,994 filed May 9, 2018, all of which are incorporated herein by reference in their entirety.

STATEMENT REGARDING FEDERALLY FUNDED RESEARCH

This invention was made with government support under HG008935 awarded by the National Institutes of Health. The government has certain rights in the invention.

BACKGROUND OF THE INVENTION

A. Field of the Invention

Embodiments generally concern molecular and cellular biology. In particular, embodiments are directed to methods and composition for labeling nucleic acids.

B. Description of Related Art

Knowledge of RNA folding is critical to understanding the function of various RNA species (Wan et al., *Nat. Rev. Genet.* 12:641-55, 2011). Chemical probes have played key roles in transcriptome-wide RNA secondary structure studies (Kubota et al., *Nat. Chem. Biol.* 11:933-41, 2015). Increasing number of methods have been developed in recent years for high-throughput RNA structure mapping (Kertesz et al., *Nature* 467:103-7, 2010; Underwood et al., *Nat. Methods* 7:995-1001, 2010; Lucks et al., *P. Natl. Acad. Sci. USA* 108:11063-68, 2011; Rouskin et al., *Nature* 505:701-5, 2014; Ding et al., *Nature* 505:696-700, 2014; Talkish et al., *RNA* 20:713-20, 2014; Wan et al., *Nature* 505:706-9, 2014; Spitale et al., *Nature* 519:486-90, 2015; Zubradt et al., *Nat. Methods* 14:75-82, 2016; Siegfried et al., *Nat. Methods* 11:959-65, 2014; Lee et al., *RNA* 23:169-74, 2017; Feng et al., *Nat. Chem. Biol.* 14:276-83, 2018). Two notable classes of chemical probes, DMS and SHAPE, enable transcriptome-wide in vivo RNA structurome mapping (Lu and Chang, *Curr. Opin. Struct. Biol.* 36:142-48, 2016). Both methods are quite effective although still with significant space for improvement; DMS is highly toxic and non-specific, and can methylate not only $m^1A$ but also $m^7G$ and $m^3A$, which potentially complicates structure determination, whereas SHAPE molecules are hydrolytically unstable and label the sugar 2'-OH instead of the base (NTP (National Toxicology Program) 2016, Report on Carcinogens, Fourteenth Edition; Research Triangle Park, NC: U.S. Department of Health and Human Services, Public Health Service.URL ntp.niehs.nih.gov/go/roc/; Merino et al., *J. Am. Chem. Soc.* 127:4223-31, 2005).

There remains a need for additional specific, non-toxic reagent(s) for rapid labeling of Watson-Crick base pairing interface under mild conditions for in vivo probing of RNA base pairing and secondary structure.

SUMMARY OF THE INVENTION

RNA secondary structure is critical to RNA regulation and function. Compositions and methods described herein provide a solution to the problems associated with in vivo labeling of nucleic acids that can be used, for example, to query RNA secondary or tertiary structure. In particular, reagents and methods are provided that allow fast and reversible labeling of single-stranded nucleic acids in live cells. By way of example, the inventors have discovered a process to reversibly label single-stranded guanine bases in live cells, which results in an effective in vivo method for transcriptome-wide RNA secondary structure mapping and RNA G-quadruplex prediction.

$N_3$-kethoxal or click chemistry kethoxal derivatives ("kethoxal derivatives") have been developed that efficiently label single-stranded DNAs and/or RNAs in live cells by reacting with the Watson-Crick interface of guanine bases. The labelling product can be further functionalized and enriched, for example using biotin/biotin binding partner. Sequencing of $N_3$-kethoxal or kethoxal derivative labelled DNA (ssDNA-seq) provides a genome-wide map of single-stranded DNA for the first time, which reveals widespread transcription dynamics. ssDNA-seq also has great potential to be used to study other biological processes in which ssDNA is involved, such as DNA replication and DNA double-strand break (DSB) formation. Experimentally, ssDNA-seq adopts a simple 3-step protocol, which makes it user-friendly and potentially works with low amount input materials. The combination of $N_3$-kethoxal or kethoxal derivative labeling and crosslinking enables the detection of RNA intermolecular or intramolecular interactions such as RNA secondary structures, RNA-RNA interactions, RNA-protein interactions and the like, as well as providing RNA exposure information. Involving a photo-activatable DBCO molecule enables in situ RNA labeling by light, which helps to study RNA metabolism in specific loci of interest.

$N_3$-kethoxal- or kethoxal derivative-assisted nucleic acid labeling methods can serve as tools to study gene expression processes, including transcription, replication, RNA metabolism, etc. $N_3$-kethoxal or kethoxal derivatives can also provide a platform for developing other nucleic acid-related technologies in both high-throughput and loci-specific manners. The labeling of ssDNA and in situ capture of all active transcription is contemplated, for use not only as key research reagent but also clinical tests. RNA-seq may not be needed if the compositions and/or methods described herein are used to capture all transcription so no RNA handling is required in clinical settings.

Described herein is a $N_3$-kethoxal or kethoxal derivative reagent that allows fast and reversible labeling of single-stranded guanine bases in live cells. The Keth-seq approach provides an effective in vivo method for transcriptome-wide RNA secondary structure mapping and RNA G-quadruplex prediction.

Certain embodiments are directed to compounds having the general formula:

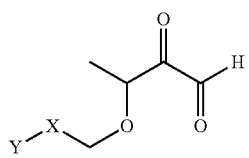

FORMULA II wherein, Y can be a click chemistry moiety selected from alkynes, azides, strained alkynes, dienes, dieneophiles, alkoxyamines, carbonyls, phosphines, hydrazides, thiols, and alkenes; and X can be a linker. In certain aspects the click chemistry moiety (Y) is azide. The linker (X) can be a C1, C2, C3, C4, C5, C6, C7, C8, C9, to C10 alkyl (one or more embodiments can be specifically excluded) or polyethylene glycol linker. In certain aspects the linker (X) is $CH_2$. In certain aspects, X can be a click chemistry moiety selected from alkynes, azides, strained alkynes, dienes, dieneophiles, alkoxyamines, carbonyls, phosphines, hydrazides, thiols, and alkenes; and Y can be a linker. In certain aspects the click chemistry moiety (X) is azide. The linker (Y) can be a C1, C2, C3, C4, C5, C6, C7, C8, C9, to C10 (one or more embodiments can be specifically excluded) alkyl or polyethylene glycol linker. In certain aspects the linker (Y) is $CH_2$.

Other embodiments are directed to a compound having the formula:

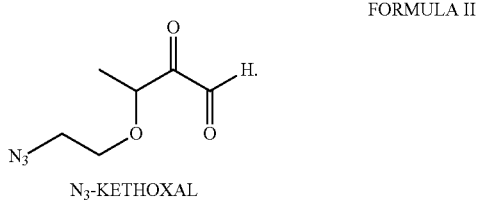

FORMULA II $N_3$-KETHOXAL

Certain embodiments are directed to methods for labeling a guanine base comprising, contacting a guanine to be labeled with a compound of Formula I or Formula II forming a reaction mixture and incubating the reaction mixture at or about 30, 31, 32, 33, 34, 35, 36, 37, 38, 39 to 40° C. or more (one or more embodiments can be specifically excluded) for at least 1, 2, 3, 4, 5, 6, 7, 8, 9, 10 or more minutes (one or more embodiments can be specifically excluded). In certain aspects the compound is $N_3$-kethoxal (Formula II). In certain aspects, the guanine is further comprised in polynucleotide. The polynucleotide can be a ribonucleic acid (RNA) or a deoxyribonucleic acid (DNA). In certain aspects the RNA is an RNA transcript.

Certain embodiments are directed to methods for labeling a single stranded nucleic acid in a cell comprising one: (i) contacting a target cell with a compound of Formula I or Formula II forming a treated cell comprising a nucleic acid having kethoxal derivative labeled guanine bases; (ii) contacting the treated cell with a crosslinking moiety comprising at least two click chemistry reactive moieties and a tag, wherein the crosslinking moiety crosslinks two proximal kethoxal derivative labeled guanines forming a crosslinked nucleic acid; and (iii) fragmenting and isolating the crosslinked nucleic acid using a reagent with an affinity for the tag. In certain aspects, the tag is biotin. The reagent with an affinity for the tag can be streptavidin. In certain aspects, the click chemistry reactive moieties are dibenzocyclooctyne moieties. The crosslinked nucleic acid can comprise two or more nucleic acids. In certain aspects, the crosslinked nucleic acid is RNA or DNA, or both RNA and DNA.

Embodiments may involve 1, 2, 3 or more steps for labeling a single stranded nucleic acid in a cell such as: (i) contacting a target cell with a compound of Formula I or Formula II forming a treated cell comprising a nucleic acid having kethoxal derivative labeled guanine bases; (ii) contacting the treated cell with a crosslinking moiety comprising at least two click chemistry reactive moieties and a tag, wherein the crosslinking moiety crosslinks two proximal kethoxal derivative labeled guanines forming a crosslinked nucleic acid; and (iii) fragmenting and isolating the crosslinked nucleic acid using a reagent with an affinity for the tag. In certain aspects, the tag is biotin. The reagent with an affinity for the tag can be streptavidin. In certain aspects, the click chemistry reactive moieties are dibenzocyclooctyne moieties. The crosslinked nucleic acid can comprise two or more nucleic acids. In certain aspects, the crosslinked nucleic acid is RNA or DNA, or both RNA and DNA.

Certain embodiments are directed to methods for in vivo transcriptome-wide RNA secondary structure mapping and RNA G-quadruplex prediction comprising the steps of: (a) labeling a nucleic acid in vivo with a kethoxal click chemistry derivative; (b) biotinylating the nucleic acid; (c) fragmenting the labeled and biotinylated nucleic acid; (d) synthesize complementary DNA from the fragmented/biotinylated nucleic acid; (e) isolate cDNA associated with biotinylated nucleic acid; (f) separating cDNA based on size; (g) perform cyclization of the cDNA to form a cyclized cDNA library; and (h) amplifying the cyclized cDNA library. In certain aspects, cyclization of cDNA is performed by contacting the cDNA with a single-stranded DNA ligase. In a further aspect, amplifying the cyclized cDNA library can be by polymerase chain reaction (PCR) or other nucleic acid amplification technique.

Embodiments may involve 1, 2, 3, 4, 5, 6, 7, or more steps (or any range there between) for in vivo transcriptome-wide RNA secondary structure mapping and RNA G-quadruplex prediction, such as: (a) labeling a nucleic acid in vivo with a kethoxal click chemistry derivative; (b) biotinylating the nucleic acid; (c) fragmenting the labeled and biotinylated nucleic acid; (d) synthesize complementary DNA from the fragmented/biotinylated nucleic acid; (e) isolate cDNA associated with biotinylated nucleic acid; (f) separating cDNA based on size; (g) perform cyclization of the cDNA to form a cyclized cDNA library; and (h) amplifying the cyclized cDNA library. In certain aspects, cyclization of cDNA is performed by contacting the cDNA with a single-stranded DNA ligase. In a further aspect, amplifying the cyclized cDNA library can be by polymerase chain reaction (PCR) or other nucleic acid amplification technique.

Certain embodiments are directed to kethoxal or kethoxal derivative chromatin crosslinking followed by DNA sequencing to analyze protein interactions with RNA (CLIP-seq methods). In certain aspects the method comprises (a) contacting a RNA-binding target or protein target in proximity to RNA with a kethoxal or a kethoxal derivative that is optionally directly or indirectly coupled to an avidity tag; (b) exposing the target/kethoxal or kethoxal derivative mixture to an activator to activate cross-linking and forming a cross-linked target/kethoxal or kethoxal derivative complex; (c) contacting the target with an affinity agent that binds a RNA-binding protein or protein target in proximity to RNA, wherein the affinity agent is optionally coupled to an avidity tag modification agent, wherein the avidity tag modification agent when brought in proximity to an avidity tag modifies the avidity tag forming an isolatable chromatin/scaffold complex; (d) isolating the target/kethoxal or kethoxal derivative complexes via the avidity tag; and (e) identify portions of the RNAs that are associated linked with the isolatable target/kethoxal or kethoxal derivative complex. In certain aspects the avidity tag is a biotinylated substrate and the avidity tag modification agent is a biotin-protein ligase.

Embodiments may involve 1, 2, 3, 4, 5 or more steps (one or more steps can be specifically excluded) such as: (a) contacting a RNA-binding target or protein target in proximity to RNA with a kethoxal or a kethoxal derivative that is optionally directly or indirectly coupled to an avidity tag; (b) exposing the target/kethoxal or kethoxal derivative mixture to an activator to activate cross-linking and forming a cross-linked target/kethoxal or kethoxal derivative complex; (c) contacting the target with an affinity agent that binds a RNA-binding protein or protein target in proximity to RNA, wherein the affinity agent is optionally coupled to an avidity tag modification agent, wherein the avidity tag modification agent when brought in proximity to an avidity tag modifies the avidity tag forming an isolatable chromatin/scaffold complex; (d) isolating the target/kethoxal or kethoxal derivative complexes via the avidity tag; and (e) identify portions of the RNAs that are associated linked with the isolatable target/kethoxal or kethoxal derivative complex. In certain aspects the avidity tag is a biotinylated substrate and the avidity tag modification agent is a biotin-protein ligase.

Certain embodiments are directed to methods for synthesizing azido-kethoxal ($N_3$-kethoxal) comprising the following steps: (a) producing a 2-(2-azidoethoxy)propanoic acid intermediate by (i) combining Sodium hydride with 2-azidoethanol in tetrahydrofuran (THF) to form a first intermediate mixture, (ii) adding ethyl 2-bromopropionate to the first intermediate mixture to form a first reaction mixture, (iii) incubating the first reaction mixture under nitrogen ($N_2$) atmosphere at room temperature forming 2-(2-azidoethoxy)propanoic acid, (iv) quenching the reaction with water, (v) adding 2-(2-azidoethoxy)propanoic acid to a LiOH aqueous solution and incubating at room temperature, and (vi) washing, isolating, and drying 2-(2-azidoethoxy)propanoic acid over anhydrous $Na_2SO_4$; (b) producing a 3-(2-azidoethoxy)-1-diazopentane-2-one intermediate by (i) dissolving 2-(2-azidoethoxy)propanoic acid in anhydrous $CH_2Cl_2$ and dimethylformamide (DMF), (ii) adding oxalyl chloride and stirring at room temperature, (iii) removing the solvent and excess oxalyl chloride forming a residue, (iv) dissolving the residue in anhydrous $CH_3CN$ and (Trimethylsilyl)diazomethane, (v) adding diethyl ether dropwise forming a second reaction mixture, (vi) stirring the second reaction mixture at 0° C. overnight, (vii) evaporating the solvent and isolating 3-(2-azidoethoxy)-1-diazopentane-2-one; and (c) producing $N_3$-kethoxal or 3-(2-azidoethoxy)-1,1-dihydroxybutan-2-one by (i) adding 3-(2-azidoethoxy)-1-diazopentane-2-one to dimethyldioxirane in acetone (DMD-acetone) forming a third reaction mixture (ii) stirring the third reaction mixture at room temperature forming $N_3$-kethoxal or 3-(2-azidoethoxy)-1,1-dihydroxybutan-2-one, and (iii) isolating $N_3$-kethoxal or 3-(2-azidoethoxy)-1,1-dihydroxybutan-2-one.

Embodiments may involve 1, 2, 3, 4, 5, 6, 7, 8, 9, 10, 11, 12, or more steps (or any range there between) such as: (a) producing a 2-(2-azidoethoxy)propanoic acid intermediate by (i) combining Sodium hydride with 2-azidoethanol in tetrahydrofuran (THF) to form a first intermediate mixture, (ii) adding ethyl 2-bromopropionate to the first intermediate mixture to form a first reaction mixture, (iii) incubating the first reaction mixture under nitrogen ($N_2$) atmosphere at room temperature forming 2-(2-azidoethoxy)propanoic acid, (iv) quenching the reaction with water, (v) adding 2-(2-azidoethoxy)propanoic acid to a LiOH aqueous solution and incubating at room temperature, and (vi) washing, isolating, and drying 2-(2-azidoethoxy)propanoic acid over anhydrous $Na_2SO_4$; (b) producing a 3-(2-azidoethoxy)-1-diazopentane-2-one intermediate by (i) dissolving 2-(2-azidoethoxy)propanoic acid in anhydrous $CH_2Cl_2$ and dimethylformamide (DMF), (ii) adding oxalyl chloride and stirring at room temperature, (iii) removing the solvent and excess oxalyl chloride forming a residue, (iv) dissolving the residue in anhydrous $CH_3CN$ and (Trimethylsilyl)diazomethane, (v) adding diethyl ether dropwise forming a second reaction mixture, (vi) stirring the second reaction mixture at 0° C. overnight, (vii) evaporating the solvent and isolating 3-(2-azidoethoxy)-1-diazopentane-2-one; and (c) producing $N_3$-kethoxal or 3-(2-azidoethoxy)-1,1-dihydroxybutan-2-one by (i) adding 3-(2-azidoethoxy)-1-diazopentane-2-one to dimethyldioxirane in acetone (DMD-acetone) forming a third reaction mixture (ii) stirring the third reaction mixture at room temperature forming $N_3$-kethoxal or 3-(2-azidoethoxy)-1,1-dihydroxybutan-2-one, and (iii) isolating $N_3$-kethoxal or 3-(2-azidoethoxy)-1,1-dihydroxybutan-2-one. As used herein, the term "nucleobase" refers to a nitrogen containing heterocyclic moiety of a nucleotide or a nucleotide analog. Non-limiting examples of suitable nucleobases include: adenine, cytosine, guanine, thymine, uracil, 5-propynyl-uracil, 2-thio-5-propynyl-uracil, 5-methylcytosine, pseudoisocytosine, 2-thiouracil, 2-thiothymine, 2-aminopurine, N9-(2-amino-6-chloropurine), N9-(2,6-diaminopurine), hypoxanthine, N9-(7-deaza-guanine), N9-(7-deaza-8-aza-guanine) and N8-(8-aza-7-deazaadenine), including naturally-occurring and synthetic derivatives. Nucleobases useful in the various embodiments described permit attachment to and transcription of RNA molecules and furthermore, may also have attached to them a reporter moiety useful in the detection and purification of the transcribed RNA. One of skill in the art would recognize that modified forms and functional analog nucleobases are also specifically contemplated.

The term "nucleoside" and "nucleotide" refers to a compound having a pyrimidine nucleobase, for example cytosine (C), uracil (U), or thymine (T), or a purine nucleobase, for example adenine (A) or guanine (G), linked to the C-1' carbon of a "natural sugar" (i.e., -ribose, 2'-deoxyribose, and the like) or sugar analogs thereof, including 2'-deoxy and 2'-hydroxyl forms. Typically, when the nucleobase is C, U or T, the pentose sugar is attached to the N1-position of the nucleobase. When the nucleobase is A or G, the ribose sugar is attached to the N9-position of the nucleobase (Kornberg and Baker, DNA Replication, 2nd Ed., Freeman, San Francisco, Calif., (1992)). The term "nucleotide" as used herein refers to a phosphate ester of a nucleoside as a monomer unit or within a polynucleotide, e.g., triphosphate esters, wherein the most common site of esterification is the hydroxyl group attached at the C-5' position of the ribose.

"Nucleoside analog" and "nucleotide analog" refer to compounds having modified nucleobase moieties (e.g., pyrimidine nucleobase analogs and purine nucleobase analogs described below), modified sugar moieties, and/or modified phosphate ester moieties (e.g., see Scheit, Nucleoside Analogs, John Wiley and Sons, (1980); F. Eckstein, Ed., Oligonucleotides and Analogs, Chapters 8 and 9, IRL Press, (1991)). The ribose or ribose analog may be substituted or unsubstituted. Substituted ribose sugars include, but are not limited to, those riboses in which one or more of the carbon atoms, such as the 2'-carbon atom or the 3'-carbon atom, can be substituted with one or more of the same or different substituents such as —R, —OR, —NRR or halogen (e.g., fluoro, chloro, bromo, or iodo), where each R group can be independently —H, C1-C6 alkyl or C3-C14 aryl. Particularly, riboses are ribose, 2'-deoxyribose, 2',3'-dideoxyribose, 3'-haloribose (such as 3'-fluororibose or 3'-chlororibose) and 3'-alkylribose, arabinose, 2'-O-methyl ribose, and locked nucleoside analogs (see for example PCT publication WO 99/14226), although many other analogs are also known in the art.

The term "nucleic acid" as used herein can refer to the nucleic acid material itself and is not restricted to sequence information (i.e., the succession of letters chosen among the five base letters A, C, G, T, or U) that biochemically characterizes a specific nucleic acid, for example, a DNA or RNA molecule. Nucleic acids described herein are presented in a 5'→3' orientation unless otherwise indicated.

As used herein, the term "polynucleotide" refers to polymers of natural nucleotide monomers or analogs thereof, including double and single stranded deoxyribonucleotides, ribonucleotides, α-anomeric forms thereof, and the like. The terms "polynucleotide", "oligonucleotide" and "nucleic acid" are used interchangeably. Usually the nucleoside monomers are linked by internucleotide phosphodiester linkages, whereas used herein, the term "phosphodiester linkage" refers to phosphodiester bonds or bonds including phosphate analogs thereof, and include associated counterions, including but not limited to $H+$, $NH_4+$, $NR_4+$, $Na+$, if such counterions are present. A polynucleotide may be composed entirely of deoxyribonucleotides, entirely of ribonucleotides or a mixture thereof.

"RNA" refers to ribonucleic acid and is a polymeric molecule implicated in various biological roles in coding, decoding, regulation, and expression of genes. RNA plays an active role within cells by catalyzing biological reactions, controlling gene expression, or sensing and communicating responses to cellular signals. Messenger RNA carries the information for the amino acid sequence of a protein to a ribosome, through which it is translated that the protein synthesized.

The term "click chemistry" refers to a chemical philosophy introduced by K. Barry Sharpless, describing chemistry tailored to generate covalent bonds quickly and reliably by joining small units comprising reactive groups together. Click chemistry does not refer to a specific reaction, but to a concept including reactions that mimic reactions found in nature. In some embodiments, click chemistry reactions are modular, wide in scope, give high chemical yields, generate inoffensive byproducts, are stereospecific, exhibit a large thermodynamic driving force >84 kJ/mol to favor a reaction with a single reaction product, and/or can be carried out under physiological conditions. A distinct exothermic reaction makes a reactant "spring loaded". In some embodiments, a click chemistry reaction exhibits high atom economy, can be carried out under simple reaction conditions, use readily available starting materials and reagents, uses no toxic solvents or use a solvent that is benign or easily removed (preferably water), and/or provides simple product isolation by non-chromatographic methods (crystallization or distillation).

The term "click chemistry handle," as used herein, refers to a reactant, or a reactive group, that can partake in a click chemistry reaction. For example, an azide is a click chemistry handle. In general, click chemistry reactions require at least two molecules comprising complementary click chemistry handles that can react with each other. Such click chemistry handle pairs that are reactive with each other are sometimes referred to herein as partner click chemistry handles. For example, an azide is a partner click chemistry handle to a cyclooctyne or any other alkyne. Exemplary click chemistry handles suitable for use according to some aspects of this invention are described herein. Other suitable click chemistry handles are known to those of skill in the art.

The term "linker," as used herein, refers to a chemical group or molecule covalently linked to another molecule. In some embodiments, the linker is positioned between, or flanked by, two groups, molecules, or moieties and connected to each one via a covalent bond, thus connecting the two. In some embodiments, the linker is an organic molecule, group, or chemical moiety.

As used herein, the term "tag" or "affinity tag" refers to a moiety that can be attached to a compound, nucleotide, or nucleotide analog, and that is specifically bound by a partner moiety. The interaction of the affinity tag and its partner provides for the detection, isolation, etc. of molecules bearing the affinity tag. Examples include, but are not limited to biotin or iminobiotin and avidin or streptavidin. A sub-class of affinity tag is the "epitope tag," which refers to a tag that is recognized and specifically bound by an antibody or an antigen-binding fragment thereof. Examples of suitable tags include, but are not limited to, amino acids, peptides, proteins, nucleic acids, polynucleotides, sugars, carbohydrates, polymers, lipids, fatty acids, and small molecules. Other suitable tags will be apparent to those of skill in the art and the invention is not limited in this aspect. In some embodiments, a tag comprises a sequence useful for purifying, expressing, solubilizing, and/or detecting a target. In some embodiments, a tag can serve multiple functions. In some embodiments, a tag comprises an HA, TAP, Myc, 6×His, Flag, or GST tag, to name few examples. In some embodiments, a tag is cleavable, so that it can be removed. In some embodiments, this is achieved by including a protease cleavage site in the tag, e.g., adjacent or linked to a functional portion of the tag. Exemplary proteases include, e.g., thrombin, TEV protease, Factor Xa, PreScission protease, etc. In some embodiments, a "self-cleaving" tag is used.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa.

The use of the word "a" or "an" when used in conjunction with the term "comprising" in the claims and/or the specification may mean "one," but it is also consistent with the meaning of "one or more," "at least one," and "one or more than one."

The term "about" or "approximately" are defined as being close to as understood by one of ordinary skill in the art. In one non-limiting embodiment the terms are defined to be within 10%, preferably within 5%, more preferably within 1%, and most preferably within 0.5%.

The term "substantially" and its variations are defined to include ranges within 10%, within 5%, within 1%, or within 0.5%.

The term "effective," as that term is used in the specification and/or claims, means adequate to accomplish a desired, expected, or intended result.

The terms "wt. %," "vol. %," or "mol. %" refers to a weight, volume, or molar percentage of a component, respectively, based on the total weight, the total volume, or the total moles of material that includes the component. In a non-limiting example, 10 moles of component in 100 moles of material is 10 mol. % of component.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods of making and using the same of the present invention can "comprise," "consist essentially of," or "consist of" particular ingredients, components, blends, method steps, etc., disclosed throughout the specification.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

Any embodiment disclosed herein can be implemented or combined with any other embodiment disclosed herein, including aspects of embodiments for compounds can be combined and/or substituted and any and all compounds can be implemented in the context of any method described herein. Similarly, aspects of any method embodiment can be combined and/or substituted with any other method embodiment disclosed herein. Moreover, any method disclosed herein may be recited in the form of "use of a composition" for achieving the method. It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

FIG. 12A-C: Reversibility of $N_3$-kethoxal labelled RNA. (a) The schemes indicate equilibrium change of $N_3$-kethoxal-guanine reaction in the presence of excess GTP. The $N_3$-kethoxal-guanine is much easier to dissociate to original unreacted RNA with excess GTP. (b) The reversibility of $N_3$-kethoxal-labeled RNA by MALDI-TOF monitoring. The kethoxal modification was largely removed after 2 h incubation with 50 mM GTP in neutral buffer at 37° C., and was almost removed when extended to 6 h. (c) Upper: Dot blot result of $N_3$-kethoxal labelled mRNA with 50 mM GTP at 95° C. in PBS buffer (pH=7.4) during different incubation periods. Bottom: denaturing gel electrophoresis of the RNA fragments under different incubation conditions same as the Upper dot blot samples. The length of fragmented RNA was almost not affected at 95° C. within 10 mins in the presence of excess GTP.

FIG. 13A-C: The fixation of kethoxal-labeled RNA by borate buffer. (a) The vicinal diol group of the adduct of guanine-kethoxal can be bonded with borate molecule to fix the kethoxal modification. (b) The formation of the guanine-kethoxal-boron complex by MALDI-TOF detection. The adduct of the guanine-kethoxal was incubated with 4-(aminomethyl)benzenboronic acid. (c) The stability testes of the guanine-kethoxal-boron complex in the presence of borate buffer. Most guanine-kethoxal adducts were retained by borate buffer fixation while all guanine-kethoxal adducts disappeared in the absence of the borate buffer.

FIG. 14A-D: Quality control of keth-seq method. (a) RPKM correlation between replicates for $N_3$-kethoxal (left) and no-treat control (right) sample. (b) RT stopped the reads distribution of replicates for $N_3$-kethoxal, $N_3$-kethoxal-remove samples, and no-treat control samples. (c) Structure signal of in vivo and in vitro mRNA sample. (d) Overlap of known rG4 regions in mRNA and +PDS sample with structure information.

FIG. 18A-B: (a) Schematic representation of the Kethoxal-Daz CLIP. RNA is covalently crosslinked to RNA binding proteins in situ after incubation and 365 nm UV irradiation. This is followed by cell lysis and purification of the crosslinked complex. Proteins were digested and the purified RNAs were retrotranscribed and subjected to Next Generation Sequencing. (b) The molecular structure of Kethoxal-Daz.

DETAILED DESCRIPTION OF THE INVENTION

Figure 1:
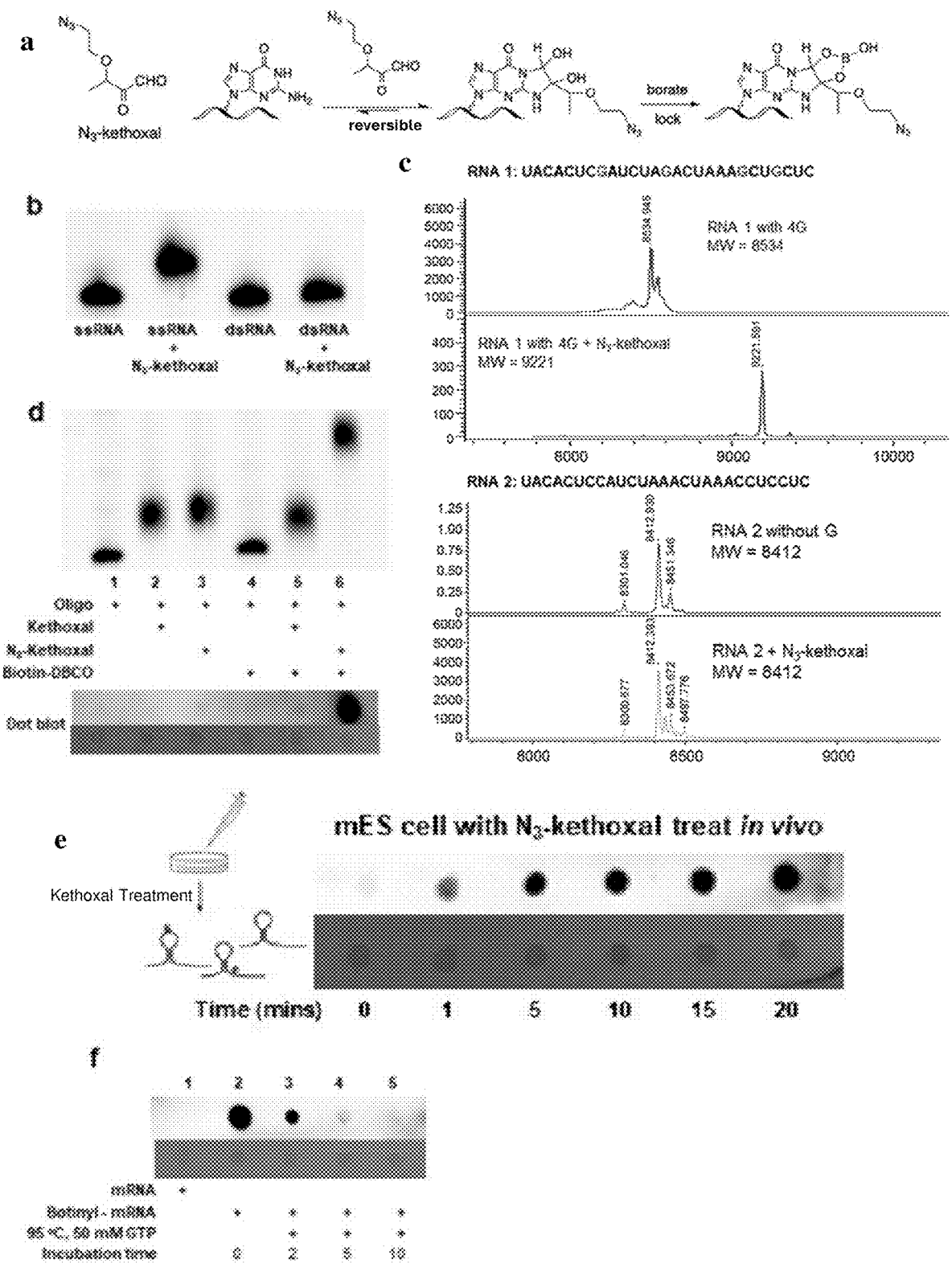
FIG. 1A-F: $N_3$-kethoxal and experimental evaluation of its selectivity, cell permeability and reversibility. (a) The structure of $N_3$-kethoxal and the reaction with guanine. (b) Denaturing gel electrophoresis demonstrating $N_3$-kethoxal only react with single-strand RNA (ssRNA). (c) Mass spectrum analysis of RNA oligoes react with $N_3$-kethoxal. In RNA 1 with four guanines, all guanines and only guanine were labelled by $N_3$-kethoxal. In RNA 2 without guanine, no $N_3$-kethoxal labelling was observed. (d) Upper: Denaturing gel electrophoresis analysis of the labelling reaction of kethoxal and $N_3$-kethoxal with FAM-RNA oligo (5'-FAM-GAGCAGCUUUAGUUUAGAUCGAGUGUA (SEQ ID NO:3, lane 1-3) and biotinylation with biotin-DBCO (lane 5, 6). Only $N_3$-kethoxal labelled RNA can be biotinylated (lane 6). Bottom: Dot blot of RNA after labelling and biotinylation reactions. Methylene blue dot results are listed as control. (e) Dot blot of isolated total RNA from mES cells which were treated by $N_3$-kethoxal with different periods, 1, 5, 10, 15, 20 mins. (f) Dot blot analysis of reversibility of $N_3$-kethoxal labelled mRNA in present of 50 mM GTP at 95° C. The $N_3$-kethoxal modification in mRNA was removed thoroughly after 10 mins incubation.

Chemical labeling of nucleic acids is extremely useful for a range of applications such as probing nucleic acid structure, nucleic acid location, nucleic acid proximity information, transcription and translation. Typical labeling strategies include metabolic labeling, in which modified nucleotides are enzymatically incorporated by polymerases during DNA/RNA synthesis, and post-synthetic labeling, which adopts synthetic small molecules to react with existing DNA/RNA. Metabolic labeling differentiates old and newly-synthesized DNA/RNA, while post-synthetic labelling could obtain selectivity to DNA/RNA with different microenvironments. Developing efficient DNA/RNA in situ labelling is still a significant challenge.

Certain embodiments are directed to the development of $N_3$-kethoxal or its derivatives as a nucleic acid labeling reagent. Data shows that the combination of $N_3$-kethoxal-based nucleic acid labeling with next generation sequencing allows genome-wide single-stranded DNA mapping, labeling and capture of RNA in situ, and probing RNA-RNA proximity information. $N_3$-kethoxal labeling has great potential to be incorporated with other technologies such as spatial-specific in situ labeling and super-resolution imaging, and screen for small molecules that bind selectively to RNA.

Single-stranded DNA (ssDNA) formation is involved in a variety of biological processes such as transcription, replication, and DNA double-strand breaks (DSB). Genome-wide mapping of ssDNA allows accurate and effective capture of active transcription at promoters, gene bodies, and enhancers. It annotates enhancers and can capture transcription events that generate transcription bubble in situ.

A unique three-stranded structure composed with a single-stranded DNA and a DNA:RNA hybrid is named R-loops (Santos-Pereira and Aguilera, *Nat. Rev. Genet.* 16:583-97, 2015). R-loops can be mapped by immunoprecipitation using a monoclonal antibody (S9.6)(Boguslawski et al., *J. Immunol. Methods* 89:123-30, 1986) or catalytic inactive RNase H (Chen et al., *Mol. Cell* 68:745-57, 2017). Mapping results help to elucidate that R-loops can affect genome stability (Hamperl et al., *Cell* 170:774-86, 2017) and regulates transcription and replication (Boque-Sastre et al., *Proc Natl Acad Sci USA.* 112:5785-90, 2015) in both physiological and pathological conditions. However, mapping ssDNA in R-loops and other processes usually relies on antibodies and needs a substantial amount of biological materials. Embodiments described herein can perform ssDNA mapping to capture R-loops.

RNA structures and interaction networks are closely linked to RNA functions and are therefore attracting growing interests. The combination of RNA labeling and high-throughput sequencing yields DMS-seq (Strobel et al., *Nat. Rev. Genet.* 19:615-34, 2018; Rouskin et al., *Nature* 505: 701-05, 2014; Ding et al., *Nature* 505:696-700, 2014) and icSHAPE (Spitale et al., *Nature* 519:486-90, 2015), which pioneered the transcriptome-wide determination of RNA secondary structures in living cells. Crosslinking RNA and proximity ligation enables in vivo RNA-RNA interaction mapping (Ramani et al., *Nat. Biotechnol.* 33:980-84, 2015; Lu et al., *Cell* 165:1267-79, 2016; Sharma et al., *Mol. Cell* 62:618-26, 2016; Aw et al., *Mol. Cell* 62, 603-17, 2016). These methods partially answer the question of how RNAs are shaped in a 2-dimensional manner, and how these structures affect RNA functions.

A. Labeling Reagents, Kethoxal Derivatives

As described herein, $N_3$-kethoxal (representative of kethoxal derivatives) is shown to react selectively with guanines at single-stranded DNA and RNA. These reactions are highly efficient under mild normal cell culture conditions, and could be directly applied to tissues. It has been found that the cell-based labeling could complete within 1, 2, 3, 4, 5, 6, 7, 8, 9, 10 min (one or more embodiments can be specifically excluded), making this probe a unique probe that has not been seen in the field to date. Its reactivity towards DNA enables the genome-wide mapping of single-stranded DNA for the first time. The formation of single-stranded DNA on gene coding regions strongly correlate with gene transcription. $N_3$-kethoxal assisted RNA labeling leads to RNA secondary structure and RNA-RNA interaction determination. Comparing RNA structures in vitro and in vivo identifies factors that mediate RNA structures dynamics in living cells, such as RNA-binding proteins and gene translation. Moreover, by combining $N_3$-kethoxal with other technologies further applications such as $N_3$-kethoxal photo-controlled in situ RNA labeling, exposed RNA mapping, single-molecular DNA/RNA imaging, small molecule RNA binder screening, etc. Any chemical moiety can be installed on a kethoxal derivative using the methods described herein. Of particular use according to some aspects of this invention are click chemistry handles. Click chemistry handles are chemical moieties that provide a reactive group that can partake in a click chemistry reaction. Click chemistry reactions and suitable chemical groups for click chemistry reactions are well known to those of skill in the art, and include, but are not limited to terminal alkynes, azides, strained alkynes, dienes, dieneophiles, alkoxyamines, carbonyls, phosphines, hydrazides, thiols, and alkenes. For example, in some embodiments, an azide and an alkyne are used in a click chemistry reaction. In certain aspects, the "click-chemistry compatible" compounds or click chemistry handles include a terminal azide functional group.

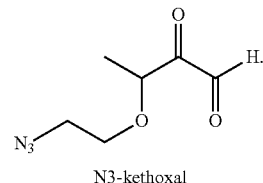

N3-kethoxal

Formula I

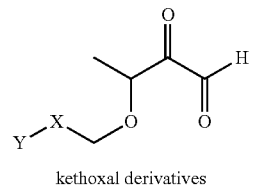

kethoxal derivatives

Formula II

In certain aspects, Y is a click chemistry compatible reactive group selected from protected thiol, alkene (including TCO) and tetrazine inverse-demand Diels-Alder, tetrazole photoclick reaction, vinyl thioether alkynes, azides, strained alkynes, dienes, dieneophiles, alkoxyamines, carbonyls, phosphines, hydrazides, thiols, and alkenes; and X is a linker (C1, C2, C3, C4, C4, C5, C6, C7, C8, C9 to C10 alkyl or more (one or more embodiments can be specifically excluded), polyethylene glycol, etc.). In other aspects, X is a click chemistry compatible reactive group selected from protected thiol, alkene (including TCO) and tetrazine inverse-demand Diels-Alder, tetrazole photoclick reaction, vinyl thioether alkynes, azides, strained alkynes, dienes, dieneophiles, alkoxyamines, carbonyls, phosphines, hydrazides, thiols, and alkenes; and Y is a linker ((C1, C2, C3, C4, C4, C5, C6, C7, C8, C9 to C10 alkyl or more (one or more embodiments can be specifically excluded), polyethylene glycol, etc.).

Definitions of specific functional groups and chemical terms are described in more detail below. For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, 5th Edition, John Wiley & Sons, Inc., New York, 2001; Larock, Comprehensive Organic Transformations, VCH Publishers, Inc., New York, 1989; Carruthers, Some Modern Methods of Organic Synthesis, 3rd Edition, Cambridge University Press, Cambridge, 1987.

The term "aliphatic," as used herein, includes both saturated and unsaturated, nonaromatic, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl," "alkynyl," and the like. Furthermore, as used herein, the terms "alkyl," "alkenyl," "alkynyl," and the like encompass both substituted and unsubstituted groups. In certain embodiments, as used herein, "aliphatic" is used to indicate those aliphatic groups (cyclic, acyclic, substituted, unsubstituted, branched or unbranched) having 1-20 carbon atoms (C1-20 aliphatic). In certain embodiments, the aliphatic group has 1-10 carbon atoms (C1-10 aliphatic). In certain embodiments, the aliphatic group has 1-6 carbon atoms (C1-6 aliphatic). In certain embodiments, the aliphatic group has 1-5 carbon atoms (C1-5 aliphatic). In certain embodiments, the aliphatic group has 1-4 carbon atoms (C1-4 aliphatic). In certain embodiments, the aliphatic group has 1-3 carbon atoms (C1-3 aliphatic). In certain embodiments, the aliphatic group has 1-2 carbon atoms (C1-2 aliphatic). Aliphatic group substituents include, but are not limited to, any of the substituents described herein, that result in the formation of a stable moiety.

The term "alkyl," as used herein, refers to saturated, straight- or branched-chain hydrocarbon radicals derived from a hydrocarbon moiety containing between one and twenty carbon atoms by removal of a single hydrogen atom. In some embodiments, the alkyl group employed in the invention contains 1-20 carbon atoms (C1-20alkyl). In another embodiment, the alkyl group employed contains 1-15 carbon atoms (C1-15alkyl). In another embodiment, the alkyl group employed contains 1-10 carbon atoms (C1-10alkyl). In another embodiment, the alkyl group employed contains 1-8 carbon atoms (C1-8alkyl). In another embodiment, the alkyl group employed contains 1-6 carbon atoms (C1-6alkyl). In another embodiment, the alkyl group employed contains 1-5 carbon atoms (C1-5alkyl). In another embodiment, the alkyl group employed contains 1-4 carbon atoms (C1-4alkyl). In another embodiment, the alkyl group employed contains 1-3 carbon atoms (C1-3alkyl). In another embodiment, the alkyl group employed contains 1-2 carbon atoms (C1-2alkyl). Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like, which may bear one or more substituents. Alkyl group substituents include, but are not limited to, any of the substituents described herein, that result in the formation of a stable moiety. The term "alkylene," as used herein, refers to a biradical derived from an alkyl group, as defined herein, by removal of two hydrogen atoms. Alkylene groups may be cyclic or acyclic, branched or unbranched, substituted or unsubstituted. Alkylene group substituents include, but are not limited to, any of the substituents described herein, that result in the formation of a stable moiety.

The term "alkenyl," as used herein, denotes a monovalent group derived from a straight- or branched-chain hydrocarbon moiety having at least one carbon-carbon double bond by the removal of a single hydrogen atom. In certain embodiments, the alkenyl group employed in the invention contains 2-20 carbon atoms (C2-20alkenyl). In some embodiments, the alkenyl group employed in the invention contains 2-15 carbon atoms (C2-15alkenyl). In another embodiment, the alkenyl group employed contains 2-10 carbon atoms (C2-10alkenyl). In still other embodiments, the alkenyl group contains 2-8 carbon atoms (C2-8alkenyl). In yet other embodiments, the alkenyl group contains 2-6 carbons (C2-6alkenyl). In yet other embodiments, the alkenyl group contains 2-5 carbons (C2-5alkenyl). In yet other embodiments, the alkenyl group contains 2-4 carbons (C2-4alkenyl). In yet other embodiments, the alkenyl group contains 2-3 carbons (C2-3alkenyl). In yet other embodiments, the alkenyl group contains 2 carbons (C2alkenyl). Alkenyl groups include, for example, ethenyl, propenyl, butenyl, 1-methyl-2-buten-1-yl, and the like, which may bear one or more substituents. Alkenyl group substituents include, but are not limited to, any of the substituents described herein, that result in the formation of a stable moiety. The term "alkenylene," as used herein, refers to a biradical derived from an alkenyl group, as defined herein, by removal of two hydrogen atoms. Alkenylene groups may be cyclic or acyclic, branched or unbranched, substituted or unsubstituted. Alkenylene group substituents include, but are not limited to, any of the substituents described herein, that result in the formation of a stable moiety.

The term "alkynyl," as used herein, refers to a monovalent group derived from a straight- or branched-chain hydrocarbon having at least one carbon-carbon triple bond by the removal of a single hydrogen atom. In certain embodiments, the alkynyl group employed in the invention contains 2-20 carbon atoms (C2-20alkynyl). In some embodiments, the alkynyl group employed in the invention contains 2-15 carbon atoms (C2-15alkynyl). In another embodiment, the alkynyl group employed contains 2-10 carbon atoms (C2-10alkynyl). In still other embodiments, the alkynyl group contains 2-8 carbon atoms (C2-8alkynyl). In still other embodiments, the alkynyl group contains 2-6 carbon atoms (C2-6alkynyl). In still other embodiments, the alkynyl group contains 2-5 carbon atoms (C2-5alkynyl). In still other embodiments, the alkynyl group contains 2-4 carbon atoms (C2-4alkynyl). In still other embodiments, the alkynyl group contains 2-3 carbon atoms (C2-3alkynyl). In still other embodiments, the alkynyl group contains 2 carbon atoms (C2alkynyl). Representative alkynyl groups include, but are not limited to, ethynyl, 2-propynyl (propargyl), 1-propynyl, and the like, which may bear one or more substituents. Alkynyl group substituents include, but are not limited to, any of the substituents described herein, that result in the formation of a stable moiety. The term "alkynylene," as used herein, refers to a biradical derived from an alkynylene group, as defined herein, by removal of two hydrogen atoms. Alkynylene groups may be cyclic or acyclic, branched or unbranched, substituted or unsubstituted. Alkynylene group substituents include, but are not limited to, any of the substituents described herein, that result in the formation of a stable moiety.

The term "carbocyclic" or "carbocyclyl" as used herein, refers to an as used herein, refers to a cyclic aliphatic group containing 3-10 carbon ring atoms (C3-10carbocyclic). Carbocyclic group substituents include, but are not limited to, any of the substituents described herein, that result in the formation of a stable moiety.

The term "heteroaliphatic," as used herein, refers to an aliphatic moiety, as defined herein, which includes both saturated and unsaturated, nonaromatic, straight chain (i.e., unbranched), branched, acyclic, cyclic (i.e., heterocyclic), or polycyclic hydrocarbons, which are optionally substituted with one or more functional groups, and that further contains one or more heteroatoms (e.g., oxygen, sulfur, nitrogen, phosphorus, or silicon atoms) between carbon atoms. In certain embodiments, heteroaliphatic moieties are substituted by independent replacement of one or more of the hydrogen atoms thereon with one or more substituents. As will be appreciated by one of ordinary skill in the art, "heteroaliphatic" is intended herein to include, but is not limited to, heteroalkyl, heteroalkenyl, heteroalkynyl, heterocycloalkyl, heterocycloalkenyl, and heterocycloalkynyl moieties. Thus, the term "heteroaliphatic" includes the terms "heteroalkyl," "heteroalkenyl," "heteroalkynyl," and the like. Furthermore, as used herein, the terms "heteroalkyl," "heteroalkenyl," "heteroalkynyl," and the like encompass both substituted and unsubstituted groups. In certain embodiments, as used herein, "heteroaliphatic" is used to indicate those heteroaliphatic groups (cyclic, acyclic, substituted, unsubstituted, branched or unbranched) having 1-20 carbon atoms and 1-6 heteroatoms (C1-20heteroaliphatic). In certain embodiments, the heteroaliphatic group contains 1-10 carbon atoms and 1-4 heteroatoms (C1-10heteroaliphatic). In certain embodiments, the heteroaliphatic group contains 1-6 carbon atoms and 1-3 heteroatoms (C1-6heteroaliphatic). In certain embodiments, the heteroaliphatic group contains 1-5 carbon atoms and 1-3 heteroatoms (C1-5heteroaliphatic). In certain embodiments, the heteroaliphatic group contains 1-4 carbon atoms and 1-2 heteroatoms (C1-4heteroaliphatic). In certain embodiments, the heteroaliphatic group contains 1-3 carbon atoms and 1 heteroatom (C1-3heteroaliphatic). In certain embodiments, the heteroaliphatic group contains 1-2 carbon atoms and 1 heteroatom (C1-2heteroaliphatic). Heteroaliphatic group substituents include, but are not limited to, any of the substituents described herein, that result in the formation of a stable moiety.

The term "heteroalkyl," as used herein, refers to an alkyl moiety, as defined herein, which contain one or more heteroatoms (e.g., oxygen, sulfur, nitrogen, phosphorus, or silicon atoms) in between carbon atoms. In certain embodiments, the heteroalkyl group contains 1-20 carbon atoms and 1-6 heteroatoms (C1-20 heteroalkyl). In certain embodiments, the heteroalkyl group contains 1-10 carbon atoms and 1-4 heteroatoms (C1-10 heteroalkyl). In certain embodiments, the heteroalkyl group contains 1-6 carbon atoms and 1-3 heteroatoms (C1-6 heteroalkyl). In certain embodiments, the heteroalkyl group contains 1-5 carbon atoms and 1-3 heteroatoms (C1-5 heteroalkyl). In certain embodiments, the heteroalkyl group contains 1-4 carbon atoms and 1-2 heteroatoms (C1-4 heteroalkyl). In certain embodiments, the heteroalkyl group contains 1-3 carbon atoms and 1 heteroatom (C1-3 heteroalkyl). In certain embodiments, the heteroalkyl group contains 1-2 carbon atoms and 1 heteroatom (C1-2 heteroalkyl). The term "heteroalkylene," as used herein, refers to a biradical derived from an heteroalkyl group, as defined herein, by removal of two hydrogen atoms. Heteroalkylene groups may be cyclic or acyclic, branched or unbranched, substituted or unsubstituted. Heteroalkylene group substituents include, but are not limited to, any of the substituents described herein, that result in the formation of a stable moiety.

The term "heteroalkenyl," as used herein, refers to an alkenyl moiety, as defined herein, which further contains one or more heteroatoms (e.g., oxygen, sulfur, nitrogen, phosphorus, or silicon atoms) in between carbon atoms. In certain embodiments, the heteroalkenyl group contains 2-20 carbon atoms and 1-6 heteroatoms (C2-20 heteroalkenyl). In certain embodiments, the heteroalkenyl group contains 2-10 carbon atoms and 1-4 heteroatoms (C2-10 heteroalkenyl). In certain embodiments, the heteroalkenyl group contains 2-6 carbon atoms and 1-3 heteroatoms (C2-6 heteroalkenyl). In certain embodiments, the heteroalkenyl group contains 2-5 carbon atoms and 1-3 heteroatoms (C2-5 heteroalkenyl). In certain embodiments, the heteroalkenyl group contains 2-4 carbon atoms and 1-2 heteroatoms (C2-4 heteroalkenyl). In certain embodiments, the heteroalkenyl group contains 2-3 carbon atoms and 1 heteroatom (C2-3 heteroalkenyl). The term "heteroalkenylene," as used herein, refers to a biradical derived from an heteroalkenyl group, as defined herein, by removal of two hydrogen atoms. Heteroalkenylene groups may be cyclic or acyclic, branched or unbranched, substituted or unsubstituted.

The term "heteroalkynyl," as used herein, refers to an alkynyl moiety, as defined herein, which further contains one or more heteroatoms (e.g., oxygen, sulfur, nitrogen, phosphorus, or silicon atoms) in between carbon atoms. In certain embodiments, the heteroalkynyl group contains 2-20 carbon atoms and 1-6 heteroatoms (C2-20 heteroalkynyl). In certain embodiments, the heteroalkynyl group contains 2-10 carbon atoms and 1-4 heteroatoms (C2-10 heteroalkynyl). In certain embodiments, the heteroalkynyl group contains 2-6 carbon atoms and 1-3 heteroatoms (C2-6 heteroalkynyl). In certain embodiments, the heteroalkynyl group contains 2-5 carbon atoms and 1-3 heteroatoms (C2-5 heteroalkynyl). In certain embodiments, the heteroalkynyl group contains 2-4 carbon atoms and 1-2 heteroatoms (C2-4 heteroalkynyl). In certain embodiments, the heteroalkynyl group contains 2-3 carbon atoms and 1 heteroatom (C2-3 heteroalkynyl). The term "heteroalkynylene," as used herein, refers to a biradical derived from an heteroalkynyl group, as defined herein, by removal of two hydrogen atoms. Heteroalkynylene groups may be cyclic or acyclic, branched or unbranched, substituted or unsubstituted.

The term "heterocyclic," "heterocycles," or "heterocyclyl," as used herein, refers to a cyclic heteroaliphatic group. A heterocyclic group refers to a non-aromatic, partially unsaturated or fully saturated, 3- to 10-membered ring system, which includes single rings of 3 to 8 atoms in size, and bi- and tri-cyclic ring systems which may include aromatic five- or six-membered aryl or heteroaryl groups fused to a non-aromatic ring. These heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocyclic refers to a non-aromatic 5-, 6-, or 7-membered ring or polycyclic group wherein at least one ring atom is a heteroatom selected from O, S, and N (wherein the nitrogen and sulfur heteroatoms may be optionally oxidized), and the remaining ring atoms are carbon, the radical being joined to the rest of the molecule via any of the ring atoms. Heterocycyl groups include, but are not limited to, a bi- or tri-cyclic group, comprising fused five, six, or seven-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Exemplary heterocycles include azacyclopropanyl, azacyclobutanyl, 1,3-diazatidinyl, piperidinyl, piperazinyl, azocanyl, thiaranyl, thietanyl, tetrahydrothiophenyl, dithiolanyl, thiacyclohexanyl, oxiranyl, oxetanyl, tetrahydrofuranyl, tetrahydropuranyl, dioxanyl, oxathiolanyl, morpholinyl, thioxanyl, tetrahydronaphthyl, and the like, which may bear one or more substituents. Substituents include, but are not limited to, any of the substituents described herein, that result in the formation of a stable moiety.

The term "aryl," as used herein, refers to an aromatic mono- or polycyclic ring system having 3-20 ring atoms, of which all the ring atoms are carbon, and which may be substituted or unsubstituted. In certain embodiments of the present invention, "aryl" refers to a mono, bi, or tricyclic C4-C20 aromatic ring system having one, two, or three aromatic rings which include, but are not limited to, phenyl, biphenyl, naphthyl, and the like, which may bear one or more substituents. Aryl substituents include, but are not limited to, any of the substituents described herein, that result in the formation of a stable moiety. The term "arylene," as used herein refers to an aryl biradical derived from an aryl group, as defined herein, by removal of two hydrogen atoms. Arylene groups may be substituted or unsubstituted. Arylene group substituents include, but are not limited to, any of the substituents described herein, that result in the formation of a stable moiety. Additionally, arylene groups may be incorporated as a linker group into an alkylene, alkenylene, alkynylene, heteroalkylene, heteroalkenylene, or heteroalkynylene group, as defined herein.

The term "heteroaryl," as used herein, refers to an aromatic mono- or polycyclic ring system having 3-20 ring atoms, of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms. Examples of heteroaryls include, but are not limited to pyrrolyl, pyrazolyl, imidazolyl, pyridinyl, pyrimidinyl, pyrazinyl, pyridazinyl, triazinyl, tetrazinyl, pyyrolizinyl, indolyl, quinolinyl, isoquinolinyl, benzoimidazolyl, indazolyl, quinolinyl, isoquinolinyl, quinolizinyl, cinnolinyl, quinazolynyl, phthalazinyl, naphthridinyl, quinoxalinyl, thiophenyl, thianaphthenyl, furanyl, benzofuranyl, benzothiazolyl, thiazolynyl, isothiazolyl, thiadiazolynyl, oxazolyl, isoxazolyl, oxadiaziolyl, oxadiaziolyl, and the like, which may bear one or more substituents. Heteroaryl substituents include, but are not limited to, any of the substituents described herein, that result in the formation of a stable moiety. The term "heteroarylene," as used herein, refers to a biradical derived from an heteroaryl group, as defined herein, by removal of two hydrogen atoms. Heteroarylene groups may be substituted or unsubstituted. Additionally, heteroarylene groups may be incorporated as a linker group into an alkylene, alkenylene, alkynylene, heteroalkylene, heteroalkenylene, or heteroalkynylene group, as defined herein. Heteroarylene group substituents include, but are not limited to, any of the substituents described herein, that result in the formation of a stable moiety.

The term "acyl," as used herein, is a subset of a substituted alkyl group, and refers to a group having the general formula —C(=O)RA, —C(=O)ORA, —C(=O)—O—C(=O)RA, —C(=O)SRA, —C(=O)N(RA)$_2$, —C(=S)RA, —C(=S)N(RA)$_2$, and —C(=S)S(RA), —C(=NRA)RA, —C(=NRA)ORA, —C(=NRA)SRA, and —C(=NRA)N(RA)$_2$, wherein RA is hydrogen; halogen; substituted or unsubstituted hydroxyl; substituted or unsubstituted thiol; substituted or unsubstituted amino; acyl; optionally substituted aliphatic; optionally substituted heteroaliphatic; optionally substituted alkyl; optionally substituted alkenyl; optionally substituted alkynyl; optionally substituted aryl, optionally substituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di heteroarylamino; or two RA groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety.

The term "acylene," as used herein, is a subset of a substituted alkylene, substituted alkenylene, substituted alkynylene, substituted heteroalkylene, substituted heteroalkenylene, or substituted heteroalkynylene group, and refers to an acyl group having the general formulae: —R$_0$—(C=X$_1$)—R$_0$—, —R—X$_2$(C=X$_1$)—R$_0$—, or —R$_0$—X$_2$(C=X$_1$)X$_3$—R$_0$—, where X$_1$, X$_2$, and X$_3$ is, independently, oxygen, sulfur, or NRr, wherein Rr is hydrogen or optionally substituted aliphatic, and R$_0$ is an optionally substituted alkylene, alkenylene, alkynylene, heteroalkylene, heteroalkenylene, or heteroalkynylene group, as defined herein. Exemplary acylene groups wherein R$_0$ is alkylene includes —(CH$_2$)T-O(C=O)(CH$_2$)T—; —(CH$_2$)T-NRr(C=O)—(CH$_2$)T—; —(CH$_2$)T-O(C=NRr)-(CH$_2$)T—; —(CH$_2$)T-NRr(C=NRr)—(CH$_2$)T—; —(CH$_2$)T-(C=O)—(CH$_2$)T—; —(CH$_2$)T-(C=NRr)-(CH$_2$)T—; —(CH$_2$)T-S(C=S)—(CH$_2$)T—; —(CH$_2$)T-NRr(C=S)—(CH$_2$)—; —(CH$_2$)T-S(C=NRr)-(CH$_2$)T—; —(CH$_2$)T-O(C=S)—(CH$_2$)T—; —(CH$_2$)T-(C=S)—(CH$_2$)T—; or —(CH$_2$)T-S(C=O)—(CH$_2$)T—, and the like, which may bear one or more substituents; and wherein each instance of T is, independently, an integer between 0 to 20. Acylene substituents include, but are not limited to, any of the substituents described herein, that result in the formation of a stable moiety.

The term "amino," as used herein, refers to a group of the formula (—NH$_2$). A "substituted amino" refers either to a mono-substituted amine (—NHRh) of a disubstituted amine (—NRh$_2$), wherein the Rh substituent is any substituent as described herein that results in the formation of a stable moiety (e.g., an amino protecting group; aliphatic, alkyl, alkenyl, alkynyl, heteroaliphatic, heterocyclic, aryl, heteroaryl, acyl, amino, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted). In certain embodiments, the Rh substituents of the di-substituted amino group (—NRh$_2$) form a 5- to 6-membered heterocyclic ring.

The term "hydroxy" or "hydroxyl," as used herein, refers to a group of the formula (—OH). A "substituted hydroxyl" refers to a group of the formula (—ORi), wherein Ri can be any substituent which results in a stable moiety (e.g., a hydroxyl protecting group; aliphatic, alkyl, alkenyl, alkynyl, heteroaliphatic, heterocyclic, aryl, heteroaryl, acyl, nitro, alkylaryl, arylalkyl, and the like, each of which may or may not be further substituted).

The term "thio" or "thiol," as used herein, refers to a group of the formula (—SH). A "substituted thiol" refers to a group of the formula (—SRr), wherein Rr can be any substituent that results in the formation of a stable moiety (e.g., a thiol protecting group; aliphatic, alkyl, alkenyl, alkynyl, heteroaliphatic, heterocyclic, aryl, heteroaryl, acyl, sulfinyl, sulfonyl, cyano, nitro, alkylaryl, arylalkyl, and the like, each of which may or may not be further substituted).

The term "imino," as used herein, refers to a group of the formula (=NRr), wherein Rr corresponds to hydrogen or any substituent as described herein, that results in the formation of a stable moiety (for example, an amino protecting group; aliphatic, alkyl, alkenyl, alkynyl, heteroaliphatic, heterocyclic, aryl, heteroaryl, acyl, amino, hydroxyl, alkylaryl, arylalkyl, and the like, each of which may or may not be further substituted).

The term "azide" or "azido," as used herein, refers to a group of the formula (—N$_3$).

The terms "halo" and "halogen," as used herein, refer to an atom selected from fluorine (fluoro, —F), chlorine (chloro, —Cl), bromine (bromo, —Br), and iodine (iodo, —I).

Synthesis of kethoxal derivatives. Kethoxal and its analogues were first reported to react with and inactivate the RNA virus since the 1950s (Staehelin, *Biochimca Biophysica Acta* 31:448-54, 1959). The 1,2-dicarbonyl group of kethoxal showed high specificity to guanine, which make it very useful in the probing of RNA secondary structure. In addition, other kethoxal derivatives, such as kethoxal bis (thiosemicarbazone)(KTS)(Booth and Sartorelli, *Nature* 210:104-5, 1966) displayed promising anticancer activity, bikethoxal (Brewer et al., *Biochemistry* 22:4303-9, 1983) demonstrated the ability to cross-link RNA and proteins within intact ribosomal 30S and 50S subunits. However, it is surprising that the synthesis of kethoxal and its derivatives are rarely reported. A review of the literature indicates that kethoxal preparation was mostly based on oxidation by selenium dioxide following purification by vacuum distillation (Brewer et al., *Biochemistry* 22:4303-9, 1983; Tiffany et al., *Journal of the American Chemical Society* 79:1682-87, 1957; Lo et al., *Journal of Labelled Compounds and Radiopharmaceuticals* 44:S654-S656, 2001). This method has several limitations. First, metal oxidation reaction always results in byproducts. Second, the excess selenium was hard to remove. Third, synthesis of kethoxal derivatives with other functional groups is difficult because the reagents with functional groups may not survive with selenium dioxide under reflux conditions. For example, studies indicate that azide- and thiol-modified kethoxal cannot be prepared by selenium dioxide oxidation. Lastly, vacuum distillation purification is not suitable for kethoxal derivatives with high-molecular weight.

Glyoxal and its analogs are sensitive to air and therefore cannot be purified by chromatography (Jiang et al., *Organic Letters* 3:4011-13, 2001). The mild oxidation of diazoketone by freshly prepared dimethyl-dioxirane (DMD) can produce a glyoxal functional group in quantitative yield (Jiang et al., *Organic Letters* 3:4011-13, 2001). In this study, azide-kethoxal was prepared through a novel synthetic strategy following a three-step synthesis (Scheme S1). The advantage of the synthetic process is its easy-to-operate and is high yield. What's more, this strategy is also convenient for the preparation of other kethoxal derivatives with various functional groups.

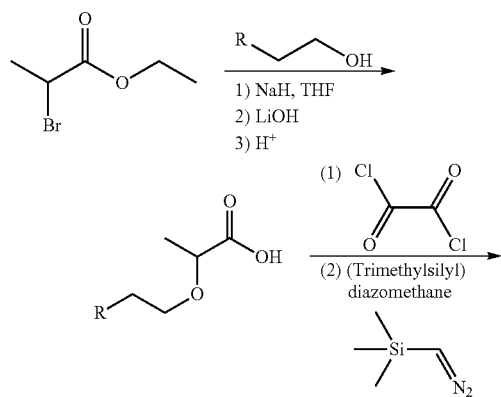

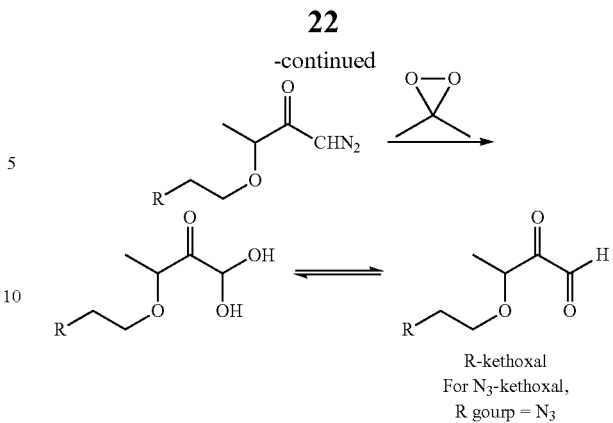

R-kethoxal
For N$_3$-kethoxal,
R gourp = N$_3$

Scheme S1—Synthesis of Kethoxal Derivatives from Various Functional Groups (R Group)

B. Kethoxal Derivatives Application and Use

N$_3$-kethoxal reacts with guanines in single-stranded DNA and RNA. Kethoxal (1,1-dihydroxy-3-ethoxy-2-butanone), is known to react with guanines specifically at N1 and N2 position at the Watson-Crick interface (Shapiro et al., *Biochemistry* 8:238-45, 1969). Due to challenges in synthesis, kethoxal has not been further functionalized and widely applied to nucleic acid labeling previously. Described herein is the development of N$_3$-kethoxal (FIG. 1a), which not only inherits the reactivity towards guanines from its parent molecule, but also contains an azido group, which serves as a bio-orthogonal handle to be further functionalized through 'click' chemistry. With MALDI-TOF analysis, it was shown that N$_3$-kethoxal efficiently labels guanines on RNA, while no reactivity was observed on other bases. It was further demonstrated the selectivity of N$_3$-kethoxal on single-stranded DNA/RNA by using gel electrophoresis. After incubation with N$_3$-kethoxal, a shift was observed on single-stranded RNA on the gel, indicating the formation of the RNA-kethoxal complex, while no such shift was detected with double-stranded RNA. It was also shown that N$_3$-kethoxal is highly cell-permeable and can label DNA and RNA in living cells within 5 min, which makes it suitable for further applications.

1. Keth-Seq for Transcriptome-Wide RNA Structure Mapping In Vivo

The N$_3$-kethoxal molecule (FIG. 1a) fulfills the requirements for the specific labeling of the N1 and N2 positions at the Watson-Crick interface of guanines in single-strand RNA (ssRNA), see above. Kethoxal has not been further modified for transcriptome-wide probing, due in part to the challenges in synthesizing kethoxal derivatives; many functional groups could not tolerate the relative harsh conditions of kethoxal synthesis. With a new synthetic scheme design described herein, azido-kethoxal (N$_3$-kethoxal) can be successfully prepared in three steps from commercially available starting materials. The azido group offers a bioorthogonal handle that can be readily modified with a biotin or any dye for enrichment or other applications (Spitale et al. *Nature* 519:486-90, 2015). In addition, the reversibility of kethoxal-guanine adduct under alkaline or heating conditions is known (Xu and Culver, *Method. Enzymol.* 468:147-65, Academic Press, 2009), and provides an additional advantage in the RT-stop-based RNA structure mapping via producing read-through controls after removing the kethoxal labels.

Figure 8:
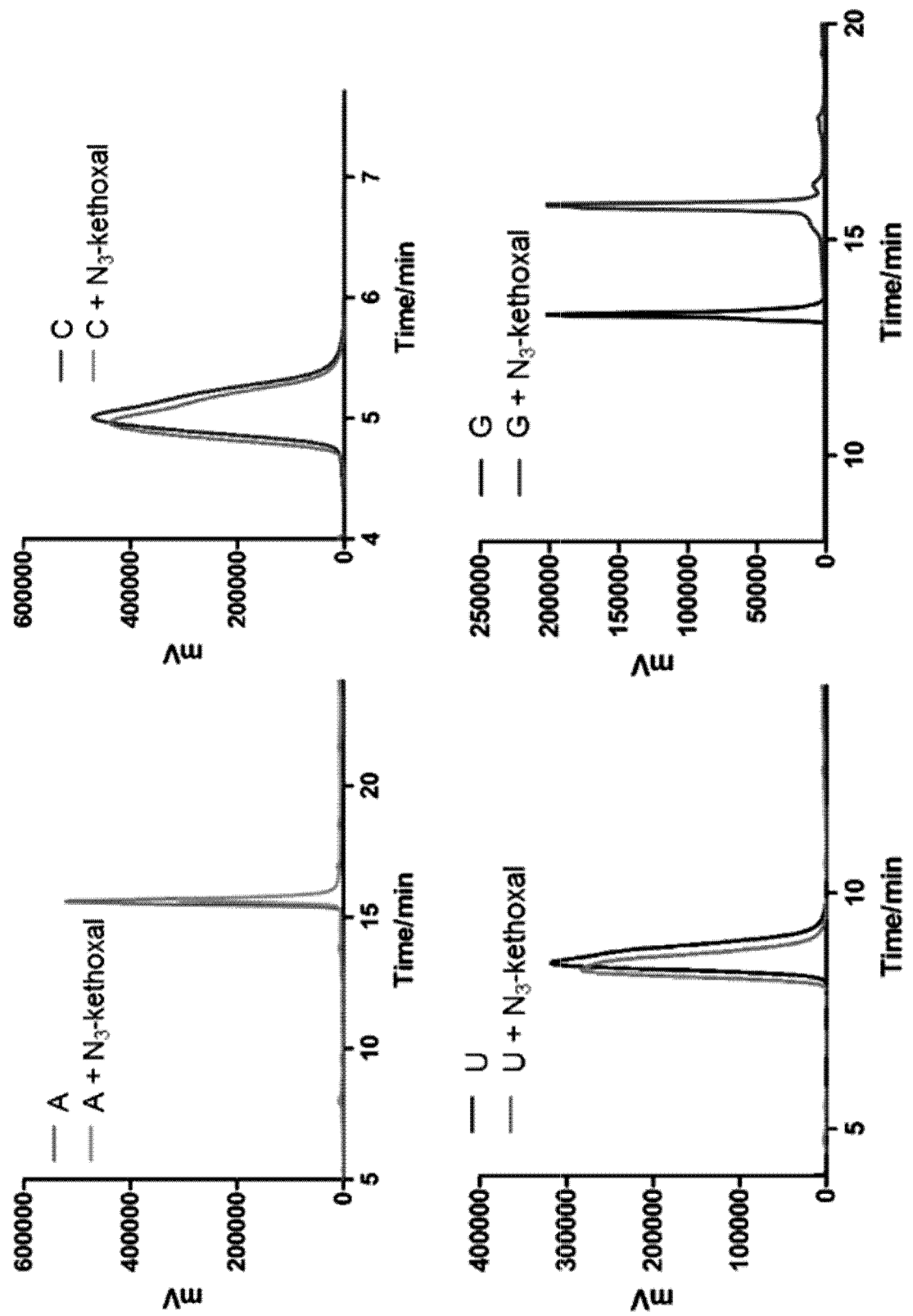
FIG. 8: The HPLC results of $N_3$-kethoxal with four RNA nucleic bases. It exhibited that $N_3$-kethoxal can only react with guanine (G) and was inert with A, C, and U.
Figure 9:
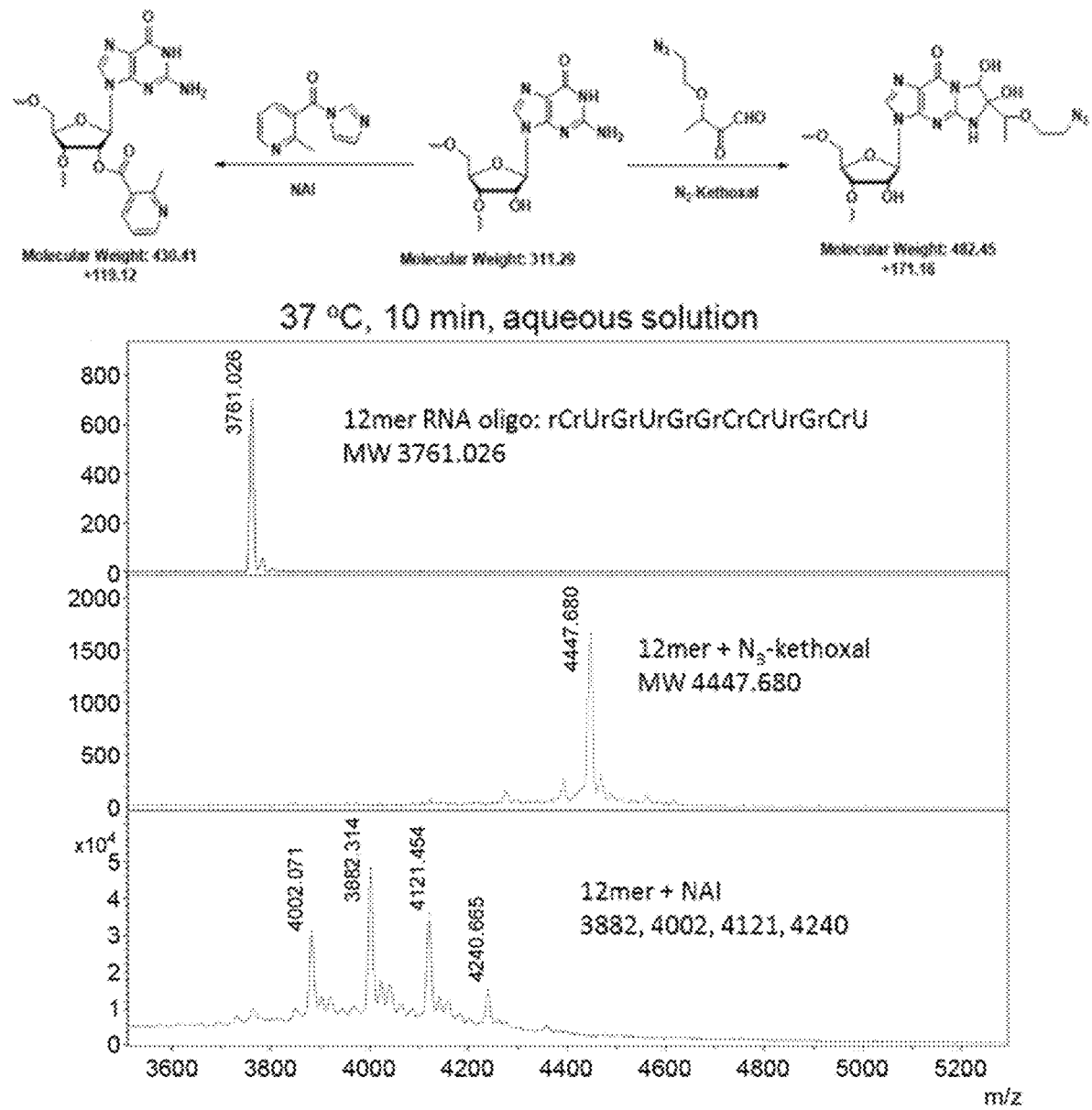
FIG. 9: The comparison of RNA reactivity of $N_3$-kethoxal and SHAPE molecular NAI. NAI was synthesized followed previous reported methods (Spitale et al., *Nature Chemical Biology* 9:18, 2012). The upper graph: the molecular weight (MW) of 12 mer RNA oligo. The middle graph: the MW of the product of 12 mer RNA oligo reacts with $N_3$-kethoxal. The bottom graph: the MW of the product of RNA oligo reacts with NAI. The results showed that all guanines (4 guanines) were modified by $N_3$-kethoxal. For the NAI reaction, some oligoes were only reacted by one NAI and some were labelled by two or three. In principle, all 2'-OH groups in ribose (12 riboses) of RNA oligo are the target of NAI. Thus, $N_3$-kethoxal showed higher reactivity to RNA.
Figure 10:
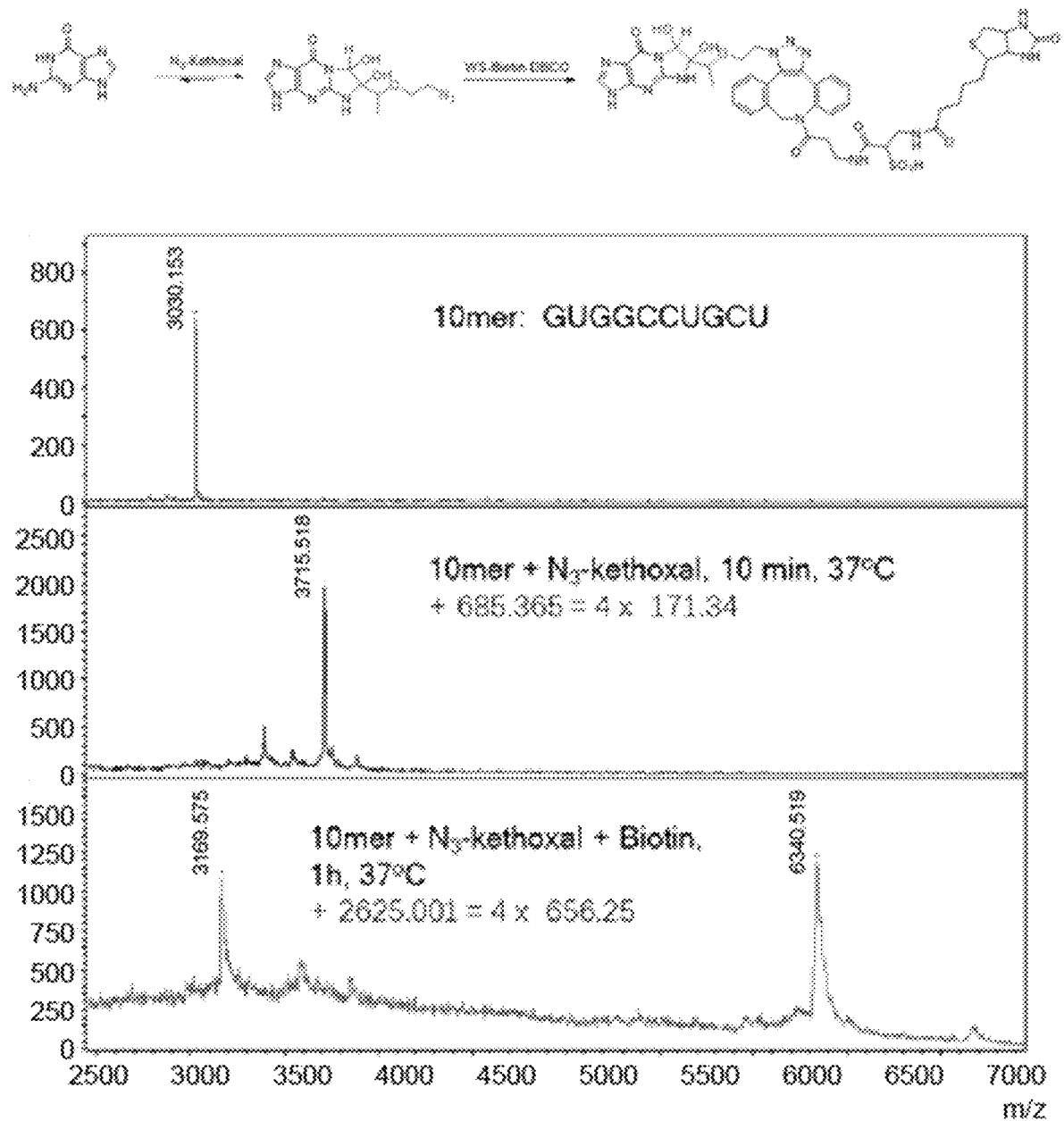
FIG. 10: The scheme (upper) and mass spectrum (bottom) analysis of the $N_3$-kethoxal labeling and biotinylation reaction in RNA. 10mer RNA with four guanines was used in this experiment.
Figure 11:
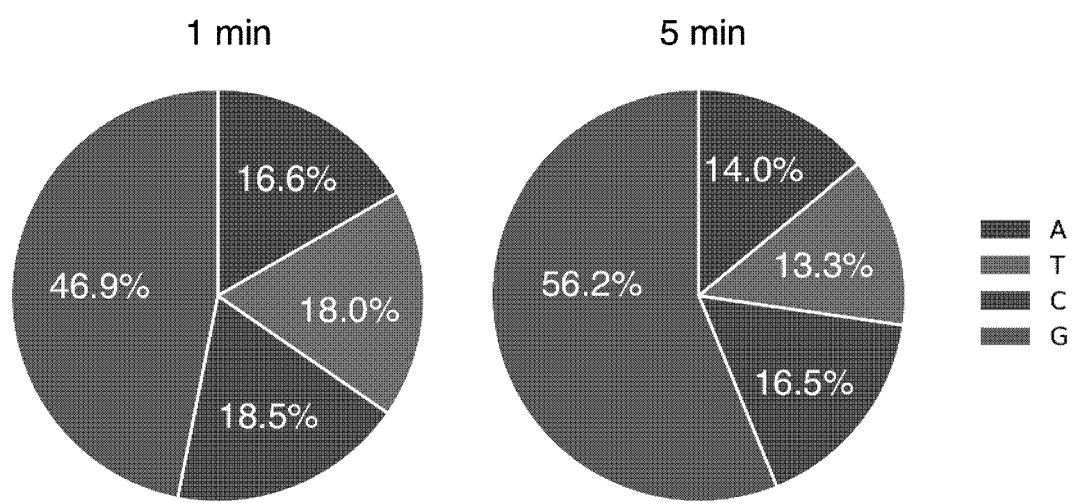
FIG. 11: The time-dependence of G labeling by $N_3$-kethoxal in the cellular state. After treatment by $N_3$-kethoxal in 1 min and 5 mins, the RNA of mES cell was isolated and performed keth-seq, which indicates that G-stop sites were increased from 1 min to 5 mins.

First, it is shown that N$_3$-kethoxal is competent for RNA structure-mapping according to the following experiment results. N$_3$-kethoxal only reacts with guanine in ssRNA and is inert with other nucleic bases (FIG. 1a, 1b; FIG. 8). All guanines in the RNA oligo were labeled by N$_3$-kethoxal by MALDI-TOF analysis (FIG. 1c). In comparison, it was found that the probe has a higher labeling activity than a commonly used SHAPE reagent, NAI (FIG. 9). The modification was biotinylated by copper-free click chemistry, as can be readily observed by gel electrophoresis, dot blot, and mass spectrum experiments (FIG. 1d and FIG. 10). The biotinylation can then be used to enrich modified nucleotides by streptavidin-conjugated beads, which is designed to increase the signal-to-noise ratio. Similar to other glyoxal derivatives, N$_3$-kethoxal can penetrate cell membranes, which is key for the feasibility of in vivo RNA structural detection. In vivo labeling efficiency was evaluated through direct addition of N$_3$-kethoxal into the culture medium of living mouse embryonic stem cells (mESCs) without any prior operations to cells. After treatment with N$_3$-kethoxal in different periods, RNA was isolated and followed on click reaction in order to perform biotinylation. The dot blot assay indicated that N$_3$-kethoxal could permeate the living cell efficiently even during one-minute incubation. The signal became saturated within five minutes of incubation, suggesting a quick cell penetration and labeling efficiency of N$_3$-kethoxal (FIG. 1e). High-throughput sequencing results confirm this phenomenon, showing that the G stop sites were increasing from 1 min to 5 mins incubation (FIG. 11). The rapid labeling ability suggest that N$_3$-kethoxal could be used in fast events such as stress response, cell cycle oscillations, etc., which cannot stand long-time incubation.

Figure 13C:
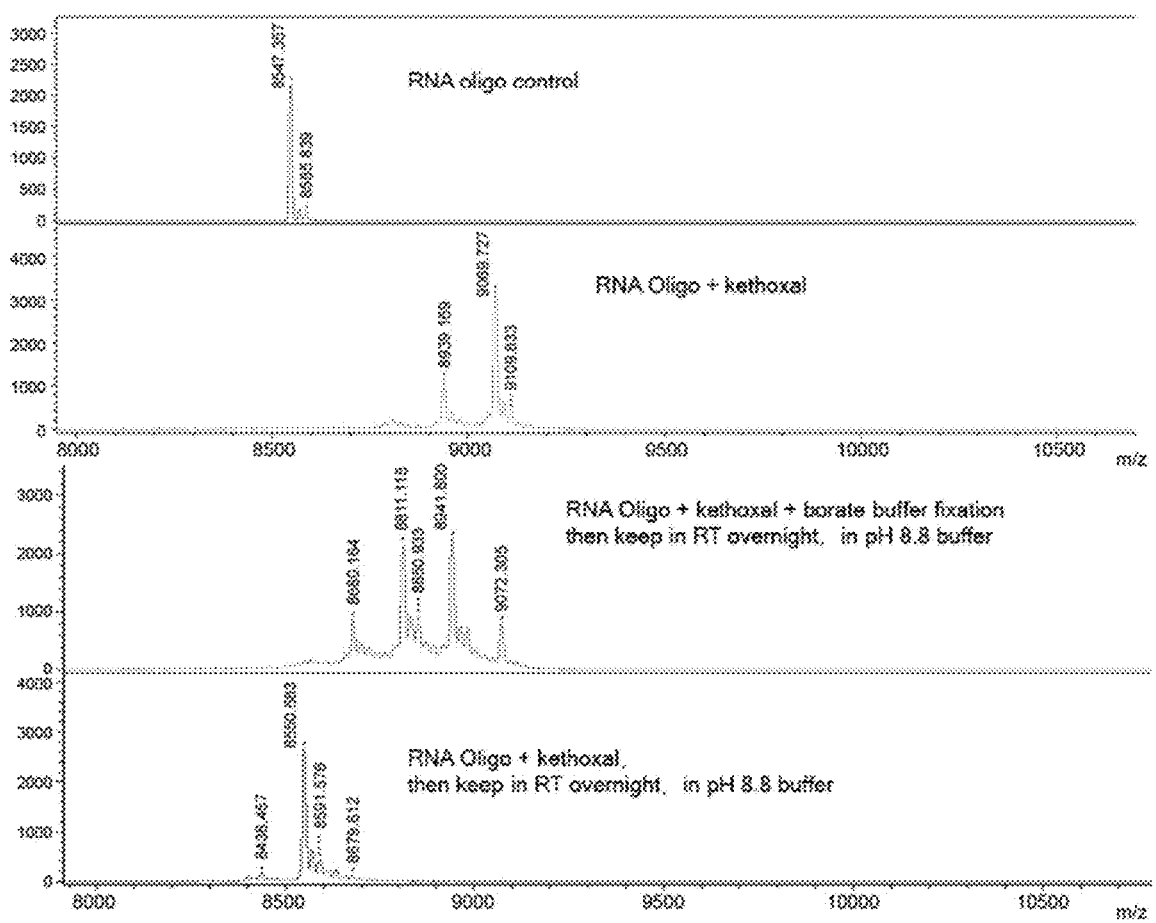

Because the kethoxal-guanine adduct is unstable under alkaline conditions (FIG. 1a), this labelling adduct could be a useful indicator to provide for an additional read-through control, which can help to remove false RT stop sites by enzyme turnover or random RNA fragments ends. Conditions were optimized in order to fully reverse the N$_3$-kethoxal modification by adding excessive guanine monomers to trap dissociated N$_3$-kethoxal, which will shift the equilibrium from N$_3$-kethoxal-RNA adducts to unmodified RNAs in a neutral buffer and within a shorter period of time (FIG. 12a). The excessive GTP was able to almost completely remove the N$_3$-kethoxal modification on the labeled RNA within 6 hours at 37° C. (FIG. 12b) or within 10 mins at 95° C. (FIG. 1f, FIG. 12c). The N$_3$-kethoxal labeled RNA could also be stabilized in borate buffer, as previously reported (FIG. 13), providing flexibility to manipulate the N$_3$-kethoxal adduct on RNA.

Figure 7:
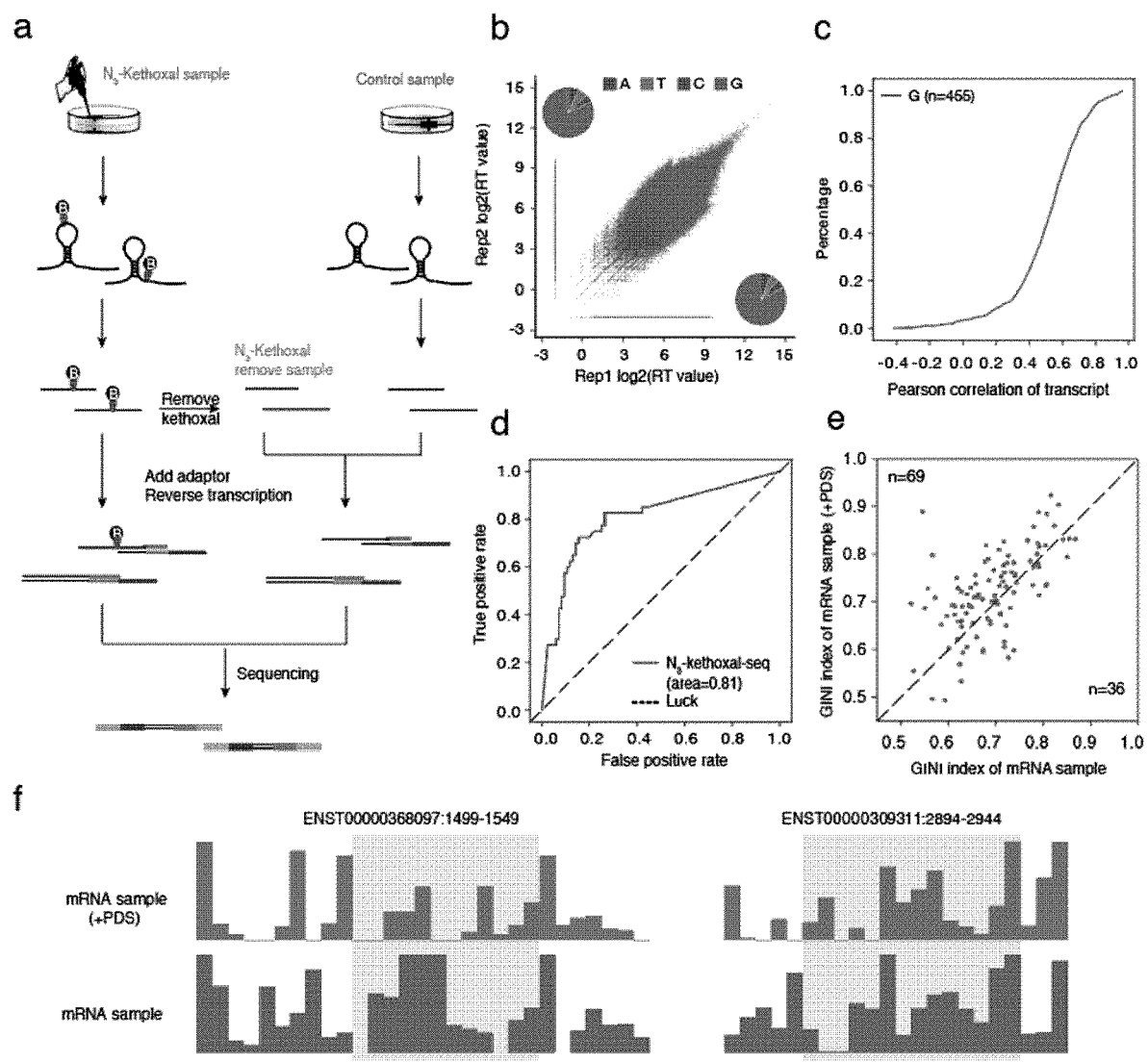
FIG. 7A-F: Keth-seq method and the profile around rG4 regions. (a) Schematic of strategy for library preparation of keth-seq. (b) Scatter plot of reverse transcription (RT) stop reads distribution between replicates for $N_3$-kethoxal sample. The inset pie plots show RT stopped base distribution for replicate 2 (upper left) and replicate 1 (bottom right). (c) Accumulation plot of correlation coefficient between keth-seq and icSHAPE for all transcript. For each common transcript, the Pearson correlation coefficient is calculated for structural signal of guanine bases. (d) Comparison between predicted 18S ribosomal RNA structure and probing structure profile. The predicted 18S rRNA structure is from RNA STRAND database (id: CRW_00356). (e) GINI index of common known rG4 regions between PDS and control sample. The rG4 regions are from Kit et. al., 2016, *Nature method* (n=13,423). 105 regions have structural information and are plotted (extended to 50 nucleotides long). (f) Two examples of structure profile around previously identified in vitro rG4 regions.
Figure 15:
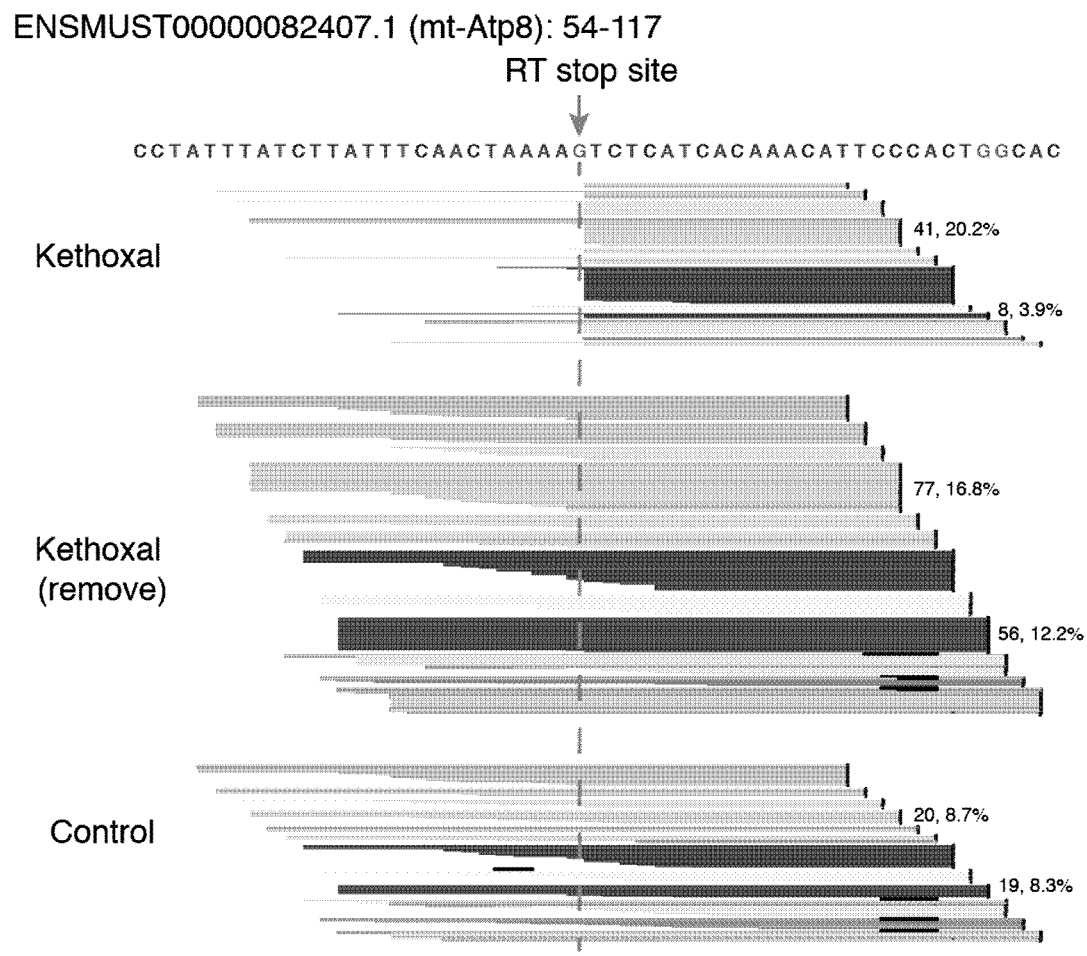
FIG. 15: An illustration of read distribution among different samples. For protein coding RNA mt-Atp8, all mapped reads whose end located within position from 97 to 108 are shown. Reads are grouped and colored by end position. Here in the $N_3$-kethoxal sample, most of the reads stopped at guanine, while in $N_3$-kethoxal-remove and no-treat control samples, the reads are distributed much more evenly, thus suggesting the high specificity of $N_3$-kethoxal molecule. For most of the read group, there are more longer reads with the same end in the removal sample than the control (for example, the highlighted cyan and red read groups). The higher ratio of the full-length read projection in the removal sample versus the control sample may indicate that the RT stopped sites with more confidence.

N$_3$-kethoxal probing was combined with deep sequencing in order to establish Keth-seq to measure RNA secondary structures in mouse ES cells (FIG. 7a). In each experiment three different RNA libraries were constructed: an N$_3$-kethoxal sample is produced from the RNA with N$_3$-kethoxal modification; an N$_3$-kethoxal-removal sample is made by erasing the N$_3$-kethoxal labelling before the reverse transcription (RT) step during library construction; and a third no-treatment control sample from intact RNA to assess the efficiency of N$_3$-kethoxal modification. The read abundance and RT stop distribution was compared between two replicates. A high correlation was observed at both RPKM (FIG. 14a) and RT level (FIG. 7b), indicative of the high quality of our sequencing data. Additionally, for the N$_3$-kethoxal sample, guanine (>80%) dominates the RT-stopped sites among all reads, but the no-treatment control sample shows no RT stop bias across all four bases (FIG. 14b). The results confirmed that the N$_3$-kethoxal molecule only modifies guanine. Results from N$_3$-kethoxal-removal sample (erasing the N$_3$-kethoxal modification) showed that RT stop reads in the guanine of this sample decreased dramatically to a level similar to the no-treatment control, indicating that N$_3$-kethoxal modification was almost completely removed in the reversal process (FIG. 14b). The complete erasing of the modified N$_3$-kethoxal molecules after pulldown can recover the real RT stop sites, which provides a potentially better matched background for Keth-seq. In fact, it was noticed that the mRNA mt-Atp8, encoding the mitochondrial ATP synthase membrane subunit 8, showed more full-length RNA fragments in the N$_3$-kethoxal-removal sample compared with the no-treatment control sample and N$_3$-kethoxal-treated sample, suggesting that the RT stopped sites could be more confidently identified using the N$_3$-kethoxal-removal sample as the control (FIG. 15).

In order to validate Keth-seq, guanine signals from Keth-seq and compared with icSHAPE were analyzed at the transcriptome level. The Pearson correlation coefficient for each transcript was calculated based on all guanine signals between Keth-seq and icSHAPE technology. About 80% of the transcripts show a positive correlation (Pearson correlation coefficient >=0.4, FIG. 7c), indicating that Keth-seq agrees well with the established icSHAPE technology. For a more direct evaluation of Keth-seq in determining RNA structure, the reactivity profile of the 18S ribosomal RNA was compared with the structure model from the RNA STRAND database (id: CRW_00356). As N$_3$-kethoxal only modifies guanine, all guanine bases were retained and measured the accuracy based on the structure model. It shows that Keth-seq reactivity profile is highly consistent with the model of 18S ribosomal RNA (AUC=0.81) (FIG. 7d). Furthermore, Keth-seq was applied in order to probe RNA structure both in vivo and in vitro for mouse ES cells. GINI index was used to measure whether a RNA is more structured or less structured. The higher the GINI index, the more structured the RNA. Consistent with previous findings, we observed that RNAs in vitro are globally more structured than that in vivo (FIG. 14c), thus validating the folding complexity of cellular RNAs and the feasible of Keth-seq for in vivo detection.

Figure 16:
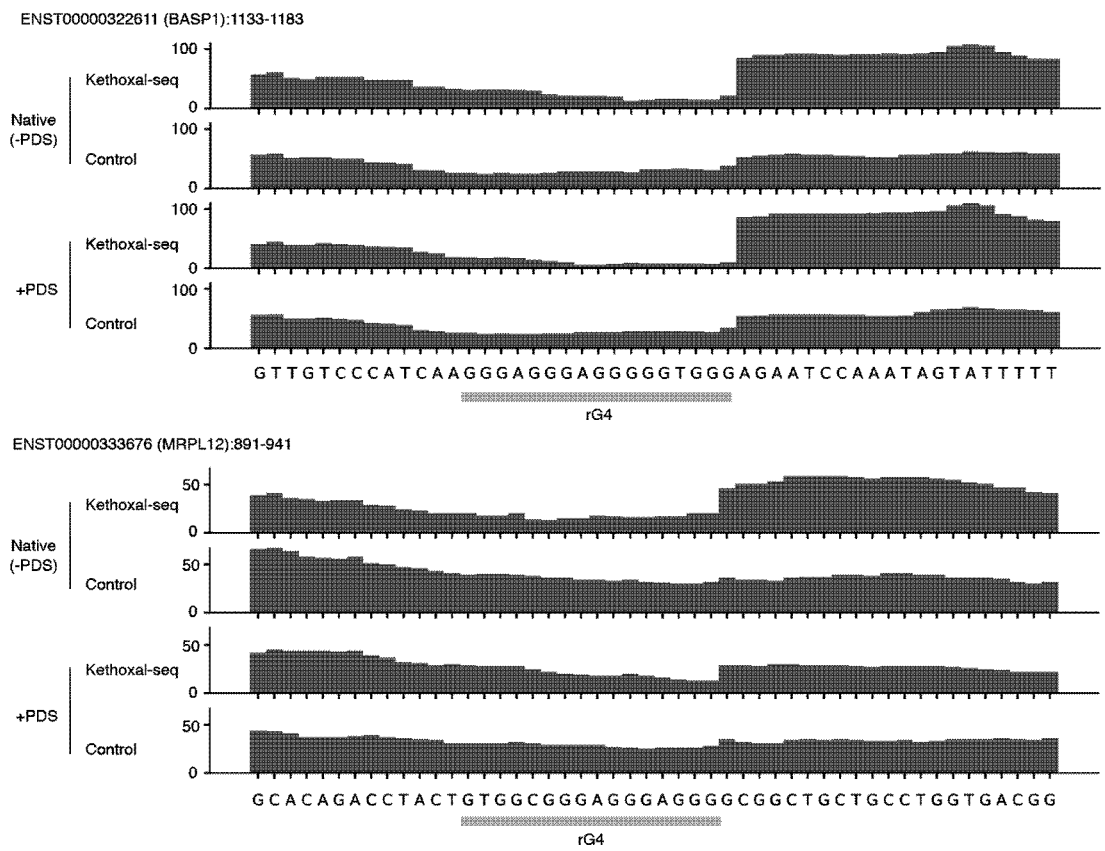
FIG. 16: Two examples showing coverage tracks around potential rG4 regions of kethoxal and control samples under both native and +PDS condition.
Figure 17:
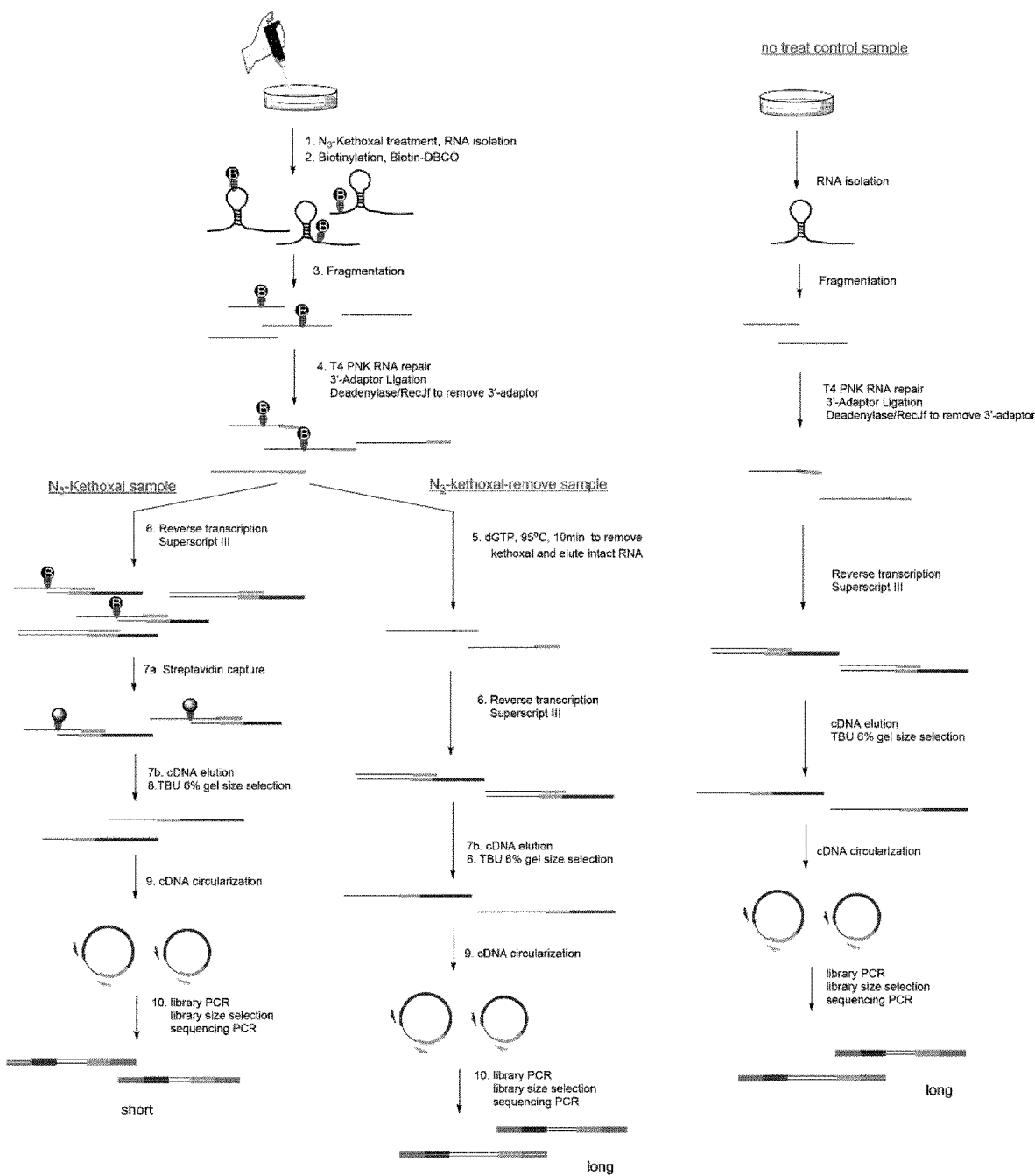
FIG. 17: Detailed flow chart of library preparation of $N_3$-kethoxal sample, $N_3$-kethoxal-remove sample, and no-treat control sample.

The characterization of RNA G-quadruplexes (rG4) in vivo remains challenging. Because of its high specificity towards guanine, the rG4 structure is a good object of N$_3$-kethoxal to probe. It has been reported that PDS treatment can induce the formation of rG4 inside cells based on immunofluorescence imaging. Keth-seq was tested for the ability to identify rG4 structures induced by PDS inside cells. Keth-seq libraries were prepared using mRNA isolated from HeLa cell with or without PDS treatment. Previously identified rG4 structure regions (n=13,423 from in vitro probing) were analyzed in the Keth-seq data, and detected hundreds of regions with potential secondary structure (FIG. 14d). Furthermore, the PDS and the control samples were compared, revealing 105 regions with formation of rG4 in both samples (Two cases in FIG. 16). As the regions that form rG4 in vivo are more double-stranded, their structures were compared in terms of GINI index. In general, the PDS sample has a higher GINI index than the control sample, suggesting that some in vitro rG4 regions are more structured under PDS treatment, and thus potentially form rG4 structures in vivo (FIG. 7e). Two examples were included where the signal in the defined rG4 regions in the PDS sample is lower than that in the control sample (FIG. 7f).

In summary, it was shown that N$_3$-kethoxal readily labels RNA and possesses excellent cell permeability. It was established Keth-seq as a new method for transcriptome-wide RNA secondary structure mapping in life cells. Because of the high selectivity and reactivity of N$_3$-kethoxal to guanine in single-stranded RNA, Keth-seq is able to discover potential rG4 regions inside cells induced by PDS. Although the finding herein only focused on the rG4 structure formation by PDS inducement.

2. Single-Stranded DNA Mapping (ssDNA-Seq)

$N_3$-kethoxal enables genome-wide single-stranded DNA mapping (ssDNA-seq). Taking advantage of the sensitivity and the selectivity of $N_3$-kethoxal towards single-stranded nucleic acids, the inventors first applied $N_3$-kethoxal to map single-stranded regions of the genome, which has not been previously achieved. Human embryonic kidney (HEK) cells were cultured in $N_3$-kethoxal-containing medium for 10 min to facilitate labelling before harvested. Genomic DNA was then purified and subjected to biotinylation reaction through "click" chemistry. Biotinylated DNA was purified and fragmented, followed by immunoprecipitation with streptavidin-coated beads. Enriched DNA and their corresponding inputs was used to make libraries, which were then sequenced and aligned.

Figure 2:
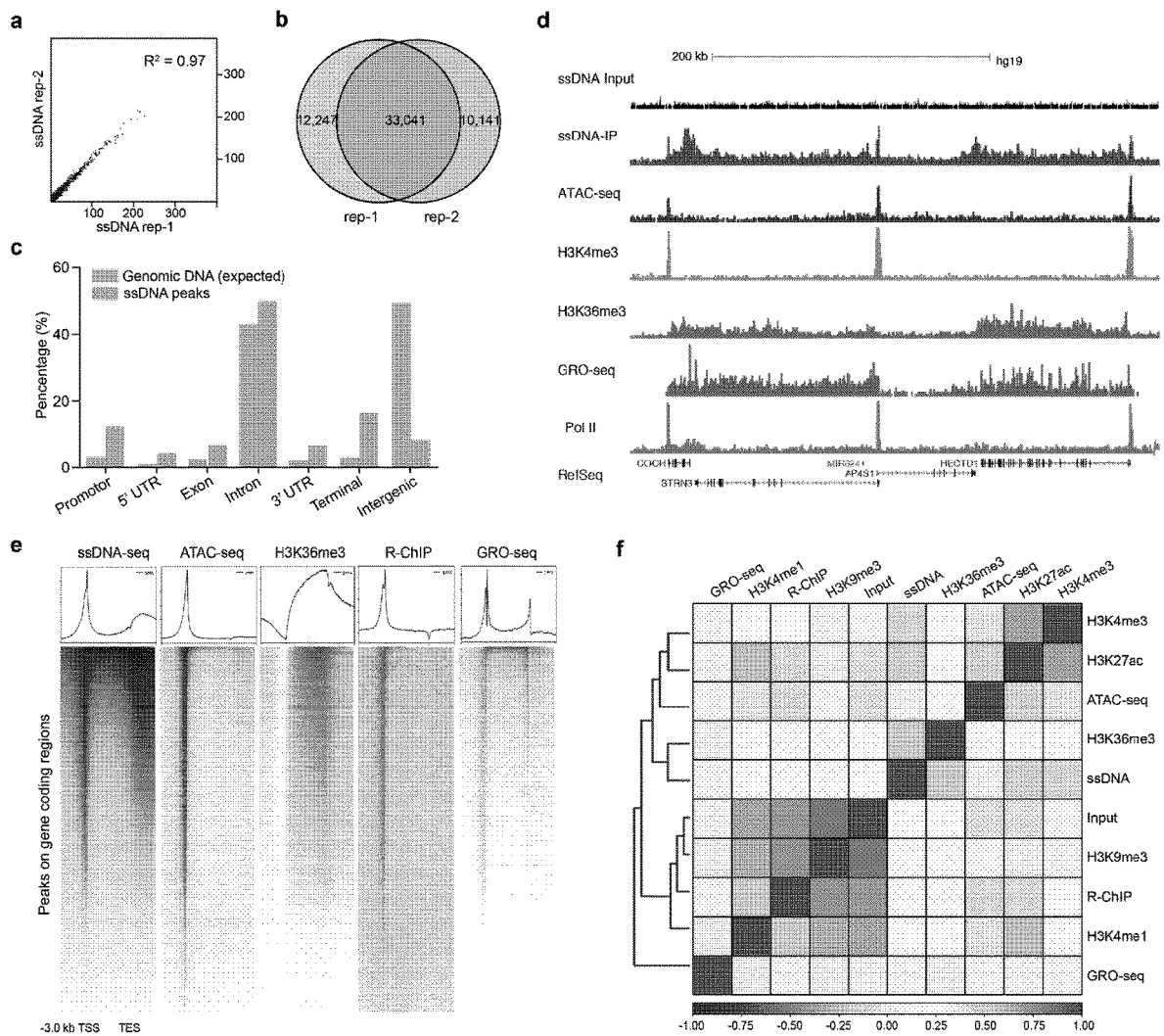
FIG. 2A-F: (a) Pearson correlation between the two individual ssDNA-seq libraries. (b) Peak numbers and their overlap between two individual ssDNA-seq libraries. (c) The distribution of ssDNA peaks on different genomic features. (d) A snapshot of aligned ssDNA-seq reads on UCSC genome browser together with corresponding ATAC-seq, H3K4me3 ChIP-seq, H3K36mes ChIP-seq, GRO-seq and Pol II ChIP-seq profiles at the same locus. (e) The distribution of ssDNA-seq peaks on gene coding regions in comparison with ATAC-seq, H3K36me3 ChIP-seq, R-ChIP and GRO-seq. (f) The correlation between ssDNA-seq with other transcription-related genome-wide sequencing assays.

Independent ssDNA-seq libraries showed high concordance ($R^2$=0.97, FIG. 2a). More than 40,000 peaks were detected in both replicates, with more than 70% (33,041) overlap between replicates (FIG. 2b). Mapped reads were enriched at gene coding areas and relatively depleted at intergenic regions (FIG. 2c). Moreover, ssDNA reads form sharp and strong peaks near transcription starting sites (TSS); in contrast, peaks at gene bodies are weaker and evenly distributed; a broad peak forms near the 3' end of genes with the maximum at +1.5 kb and a small drop at transcription ending sites (TES) (FIG. 2d).

Figure 3:
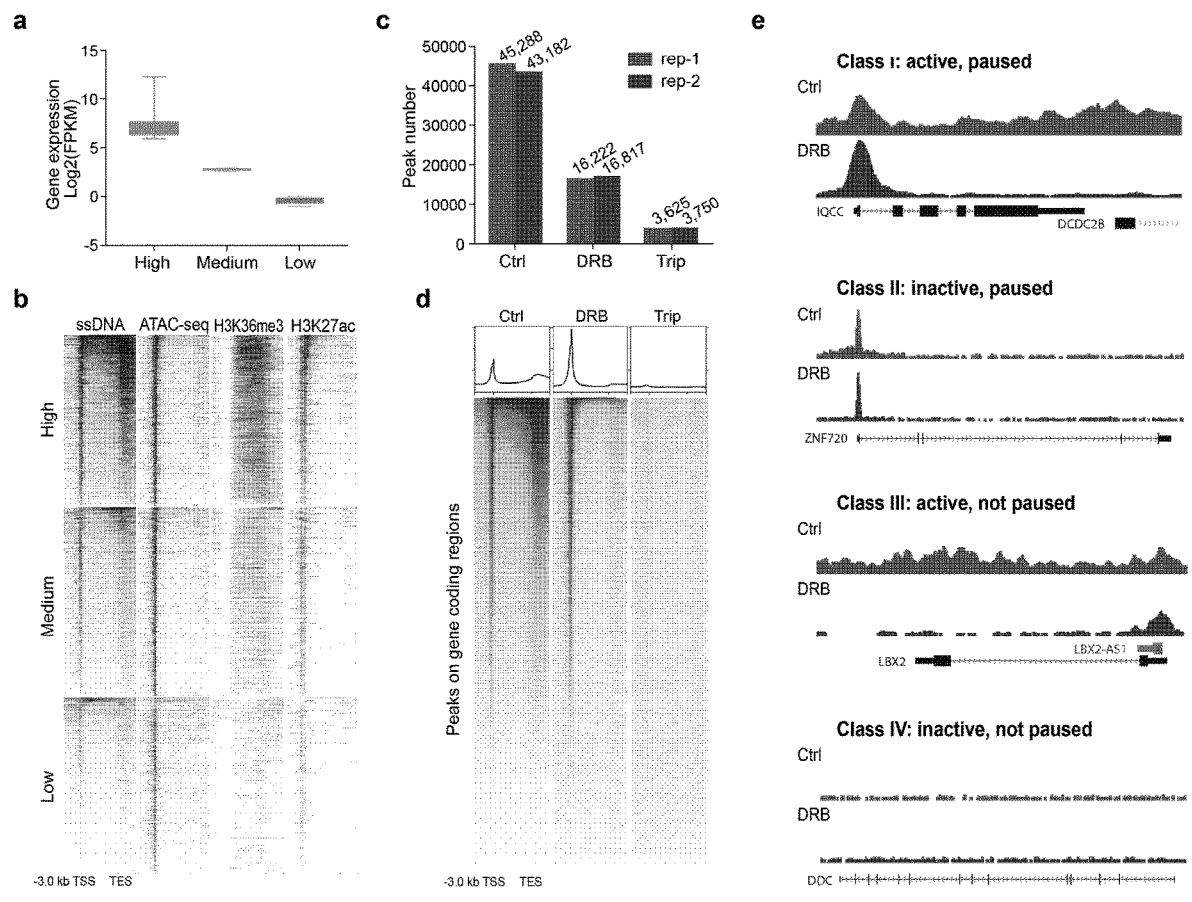
FIG. 3A-E: (a) All expressed genes are sorted into three groups with high, medium or low RNA level. (b) The ssDNA, ATAC-seq H3K36me3 and H3K27ac signals in the three groups showed in (a). (c) ssDNA peak numbers in control, DRB-treated and triptolide-treated cells (two replicate were performed for each condition, Trip=triptolide). (d) The distribution of ssDNA-seq peaks on gene coding regions in control, DRB-treated and triptolide-treated conditions. (e) All genes were classified into four groups with different Pol II pausing and activities according to their ssDNA formation under control and DRB-treated conditions. One example in each group was shown on the UCSC genome browser.

The enrichment and the unique distribution pattern of ssDNA peaks at gene coding areas incited a look closer at its correlation with transcription. The inventors compared ssDNA peaks on gene coding regions with peaks revealed by other transcription-related assays, as well as Pol II and histone modifications which defines transcription states. ssDNA peaks were shown to positively correlated with peaks detected by global run-on sequencing (GRO-seq) (Core et al., *Science* 322:1845-48, 2008) and Pol II ChIP-seq (FIG. 2d, 2e). Specifically, ssDNA peaks at proximal-promotor regions overlap well with R-loops and H3K4me3, while peaks at gene body overlap with active elongation mark H3K36me3 (FIG. 2d, 2e). Transposase-accessible chromatin using sequencing (ATAC-seq)(Buenrostro et al., *Nat. Methods.* 10:1213-18, 2013), which precisely displays the genomic location of histone modifications, was compared with ssDNA-seq on their correlations with histone modifications. ssDNA-seq correlates better than ATAC-seq with histone modifications that marks active transcription, such as H3K4me3, H3K36me3 and H3K27ac, but showed a poor correlation with the heterochromatin mark H3K9me3 (FIG. 2f). Together, these results indicate ssDNA peaks on gene coding regions correlates with transcription status.

ssDNA-seq reveals widespread transcription dynamics. To validate the relationship between ssDNA formation and transcription, RNA-seq was performed on the same cell line and sorted all expressed genes into three groups according to their RNA levels (high, medium and low, FIG. 3a). ssDNA peaks were found significantly stronger in genes with high RNA levels than those with medium or low RNA levels (FIG. 3b). As RNA-seq only reflects steady-state RNA level but cannot reveal real-time transcription states, next two Pol II inhibitors were applied, triptolide and 5,6-dichloro-1-β-D-ribofuranosylbenzimidazole (DRB), and studied corresponding ssDNA change. Triptolide triggers Pol II degradation while DRB inhibits Pol II CTD dephosporylation and therefore impedes Pol II elongation (Bensaude, *Transcription* 2:103-08, 2011). Upon DRB treatment, ssDNA peak number decreased from more than 43,000 to around 16,000 (FIG. 3c). Stronger peaks were observed at TSS while peaks on gene body and TES were eliminated, which is consistent with increased Pol II pausing and weak Pol II elongation (FIG. 3d). Triptolide resulted in a dramatic ssDNA peak number decrease to ~3,700 (FIG. 3c). As expected, most peaks on gene coding regions disappeared due to global Pol II degradation (FIG. 3d).

These results validated that ssDNA on gene coding regions is the outcome of Pol II-induced DNA double-strand open. The strength of ssDNA peaks reveals Pol II density. Strong and sharp peaks near TSS represents Pol II pausing; weak and evenly distributed reads at gene body represents Pol II elongation; the broad peaks near the 3' end represents pre-termination and poly(A) cleavage. These results indicate that ssDNA profiles enable the determination of transcription states of genes into four classes: class I, active and paused; class II, inactive and paused; class III, active and not paused; class IV, inactive and not paused (FIG. 3e).

It was also noticed a small portion of enhancers are single-stranded while the rest are not. It was hypothesized that these "single-stranded enhancers" process more capability to activate transcription.

Representative procedure for single-stranded DNA (ssDNA) mapping. One procedure for ssDNA can comprise one or more of the following steps. First step can be preparing a labeling medium by adding $N_3$-kethoxal or a kethoxal derivative to a cell culture medium. Incubating cells in the labeling medium for a desired time, at a desired temperature, under desired conditions. Transcription inhibition studies can be performed by treating cells under DRB or triptolide or equivalent reagent prior to incubating in $N_3$-kethoxal- or kethoxal derivative-containing medium. After incubation, harvesting the cells, and isolating total DNA from the cells. DNA can be suspended in $H_2O$ and in the presence of DBCO-$PEG_4$-biotin (DMSO solution) and incubated at an appropriate temperature for an appropriate time, e.g., 37° C. for 2 h. RNase A can be added to the reaction mixture and the mixture incubated for an appropriate time at an appropriate temperature, e.g., 37° C. for 15 min. 7. DNA can be recovered from the reaction mixture and used to construct libraries. Libraries can be constructed using various commercial library construction kits, for example Accel-NGS Methyl-seq DNA library kit (Swift) or Kapa Hyper Plus kit (Kapa Biosystems). The next step can include sequencing libraries, for example on a Nextseq SR80 mode and perform downstream analysis.

3. Kethoxal-Assisted RNA-RNA Interaction Mapping (KARRI)

Figure 4:
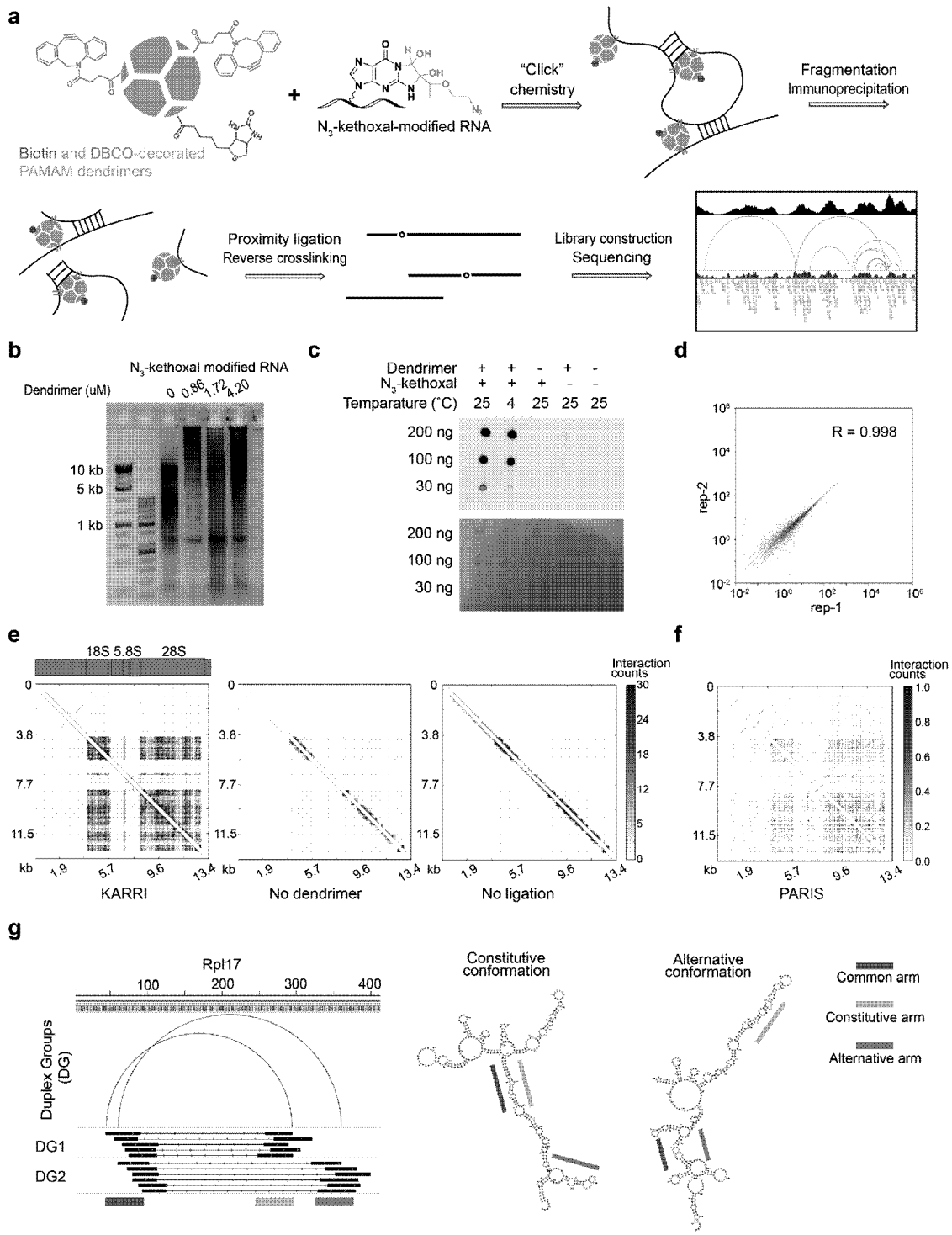
FIG. 4A-G: (a) The scheme of Kethoxal-Assisted RNA-RNA interaction (KARRI). The balls stand for PAMAM dendrimers. The dots and rods stand for the biotin and the DBCO moiety, respectively. (b)-(c) Gel electrophoresis (b) and dot blot (c) analysis of the crosslinking efficiency by DBCO and biotin decorated PAMAM dendrimers to $N_3$-kethoxal labelled RNAs. (d) Pearson correlation between the two individual KARRI libraries. (e) The interaction maps of 45S rRNA revealed by KARRI together with two control experiments with no dendrimer added or no proximity ligation performed. (f) The interaction maps of 45S rRNA revealed by PARIS. (g) KARRI reveals two alternative conformations of RPL17 mRNA.

Considering the reactivity of $N_3$-kethoxal towards RNA, kethoxal-assisted RNA-RNA interaction mapping (KARRI) was developed based on $N_3$-kethoxal labeling and dendrimer crosslinking of interacting RNA-RNA. To demonstrate KARRI mapping, formaldehyde-fixed mouse embryonic stem cells (mESC) were treated with $N_3$-kethoxal and then incubated with PAMAM dendrimers (Esfand and Tomalia, (2001) *Drug Discov. Today* 6:427-36) decorated with two dibenzocyclooctyne (DBCO) molecules and one biotin molecule at the surface (FIG. 4a). Each PAMAM dendrimer chemically crosslinks two proximal $N_3$-kethoxal labeled guanines through the "click" reaction, and provides a handle for enrichment through the biotin moiety on it. After crosslinking, RNAs were isolated, fragmented and subjected to immunoprecipitation by streptavidin beads (FIG. 4a). Proximity ligation was then performed on beads and the product RNA was used for library construction (FIG. 4a). Sequencing reads were aligned with only chimeric reads used for RNA-RNA interaction analysis.

Gel electrophoresis (FIG. 4b) and dot blot (FIG. 4c) confirmed that the crosslinking reaction between dendrimers and RNA is efficient and specific. KARRI is highly reproducible (FIG. 4d) and detects both RNA secondary structure and 3-dimensional RNA-RNA interactions. For instance, by looking at rRNA-rRNA chimeric reads, KARRI reconstitute the 2-dimensional interaction map of 45S rRNAs (FIG. 4e), which is similar with previously reported psoralen-based RNA-RNA interaction mapping method (PARIS, FIG. 4f) (Lu et al., Cell 165:1267-79, 2016). Samples prepared without dendrimer crosslinking or without proximity ligation showed very weak or undetectable signals (FIG. 4e). KARRI also detects alternative RNA structures. For example, two duplex groups (DGs) were detected in RPL17 mRNA, with one common arm exclusively interacting with two arms (constitutive, alternative), corresponding to two conflict conformations resulted from Boltzmann ensemble (FIG. 4f).

Figure 5:
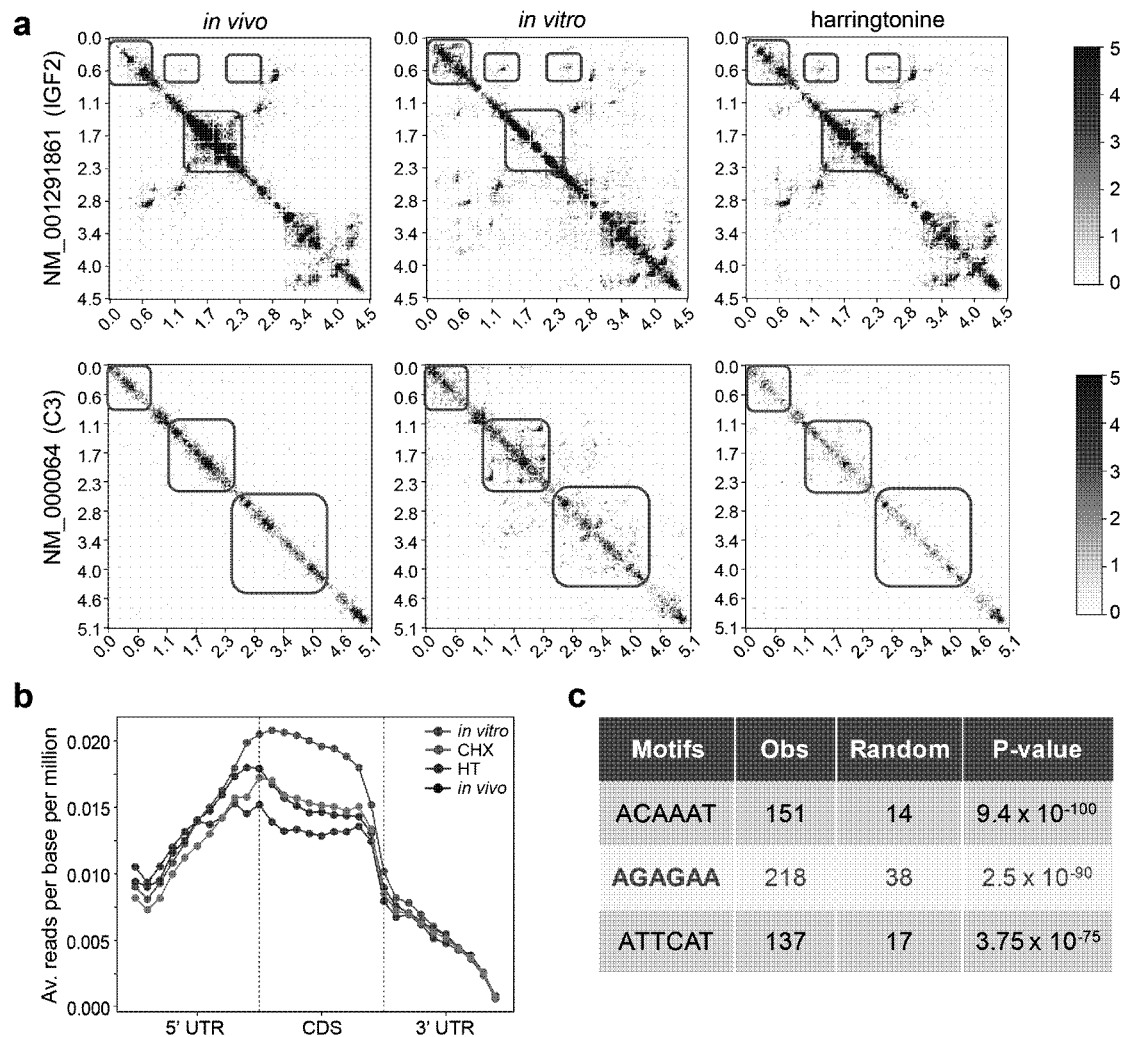
FIG. 5A-C: (a) Two examples showing KARRI detects differences between RNA secondary structures in vitro and in vivo. In harringtonine-treated cells, in vivo-specific structures were undermined while some in vitro-specific features showed up. Regions of interested are circles. (b) The metagene profile of intramolecular mRNA secondary structures in in vitro, in vivo, CHX and HT treated samples. (c) Motif analysis result of all chimeric reads of HepG2 mRNA. AGAGAA is similar with the known binding motif of eIF4AIII.

KARRI decodes in vivo RNA structure contributors. Comparing with in vitro RNA folding, RNA secondary structures and intermolecular RNA-RNA interactions are regulated by varieties of cellular factors such as RNA modifications and RNA binding proteins (RBPs) in a very complex manner (Lewis et al., Nat. Rev. Mol. Cell Bio. 18:202-10, 2017). Additional studies were performed to study how RNA structures and interactions are formed and regulated in living cells. Purified RNA was refolded in vitro and performed KARRI to compare with in vivo KARRI result. As expected, some structural features detected in vivo disappeared while some new structures showed up as thermodynamically stable RNA self-folding conformations (FIG. 5a).

RBP binding and translation are contemplated to be key contributors that result in these differences. To test this, cells were treated with two widely-used translation inhibitors, harringtonine (HT) and cycloheximide (CHX)(Ingolia et al., Cell 147:789-802, 2011), and performed KARRI experiment. Translation inhibition resulted in undermined in vivo-specific structures and increased in vitro features (FIG. 5a), indicating translation contributes to RNA secondary structure forming in live cells. This is further validated by metagene analysis. Metagene profile showed mRNA in vivo are generally less structured than in vitro refolded mRNAs at CDS, and treating cells with translation inhibitors makes mRNA structures in live cells "in-vitro-like" (FIG. 5b). After translation inhibition, mRNAs in vivo are still less structured than in vitro refolded mRNA, potentially due to the contribution from other factors such as RBPs. Indeed, motif analysis of chimeric mRNA reads identifies motifs that corresponding to the binding of motifs of know RBPs such as eIF4AIII (FIG. 5c), a core protein in mammalian exon junction complexes (EJCs) (Sauliere et al., Nat. Struct. Mol. Bio. 19:1124-31, 2012). Integrative comparison of these motifs with published eCLIP data from ENCODE (The ENCODE Project Consortium, Nature 489:57-74, 2012) is ongoing.

Procedure for kethoxal-Assisted RNA-RNA interaction (KARRI). The KARRI methods can include one or more of the following steps. Cells can be suspended in a fixative, e.g., formaldehyde solution, and incubated at room temperature with gentle rotate. The reaction can be quenched, e.g., by adding glycine. For translation inhibitor treatment, cells are treated with cycloheximide or harringtonine. Cells are collected and aliquoted. $N_3$-Kethoxal or kethoxal derivative can be diluted 1:5 using an appropriate solvent, e.g., DMSO, and incorporated into a labeling buffer ($N_3$-Kethoxal or kethoxal derivative, lysis buffer (10 mM Tris-HCl pH 8.0, 10 mM NaCl, 0.2 IGEPAL CA630) and proteinase inhibitor cocktail). Cells can be suspended in labeling buffer and cells collected after incubation. Collected cells can be washed in ice-cold lysis buffer 1, 2, 3 or more times. The cell pellet can be suspended in MeOH containing cross-linkers and the cells collected. RNA can be extracted and purified. RNA pellets can be suspended in $H_2O$, with DNase I buffer (100 mM Tris-HCl pH 7.4, 25 mM $MgCl_2$, 1 mM $CaCl_2$)), DNase I, RNase inhibitor, and incubated with gentle shaking. The mixture is then exposed to proteinase K. RNA is extracted with phenol-chloroform and purified RNA by EtOH precipitation. RNA pellets are suspended $H_2O$ and fragmentation buffer with RNase inhibitor and incubated. Fragmentation is stopped by additional of fragmentation stop buffer and the sample is put on ice to quench the reaction. Crosslinked RNA is enriched by using pre-washed Streptavidin beads. Beads are mixed with DNA and the mixture was incubated at room temperature with gentle rotate. After incubation, beads were washed. Washed beads are suspended in $H_2O$ with PNK buffer and T4 PNK, RNase inhibitor and shaken for a first incubation period, then another aliquot of T4 PNK and ATP are added and shaken for a second incubation period. Beads are washed and suspended in a ligase solution. After incubation in ligase solution the beads are washed. RNA is eluted by heating and the RNA recovered. Half of the recovered RNA is used for library construction. Libraries are sequenced and downstream analysis performed.

Figure 6:
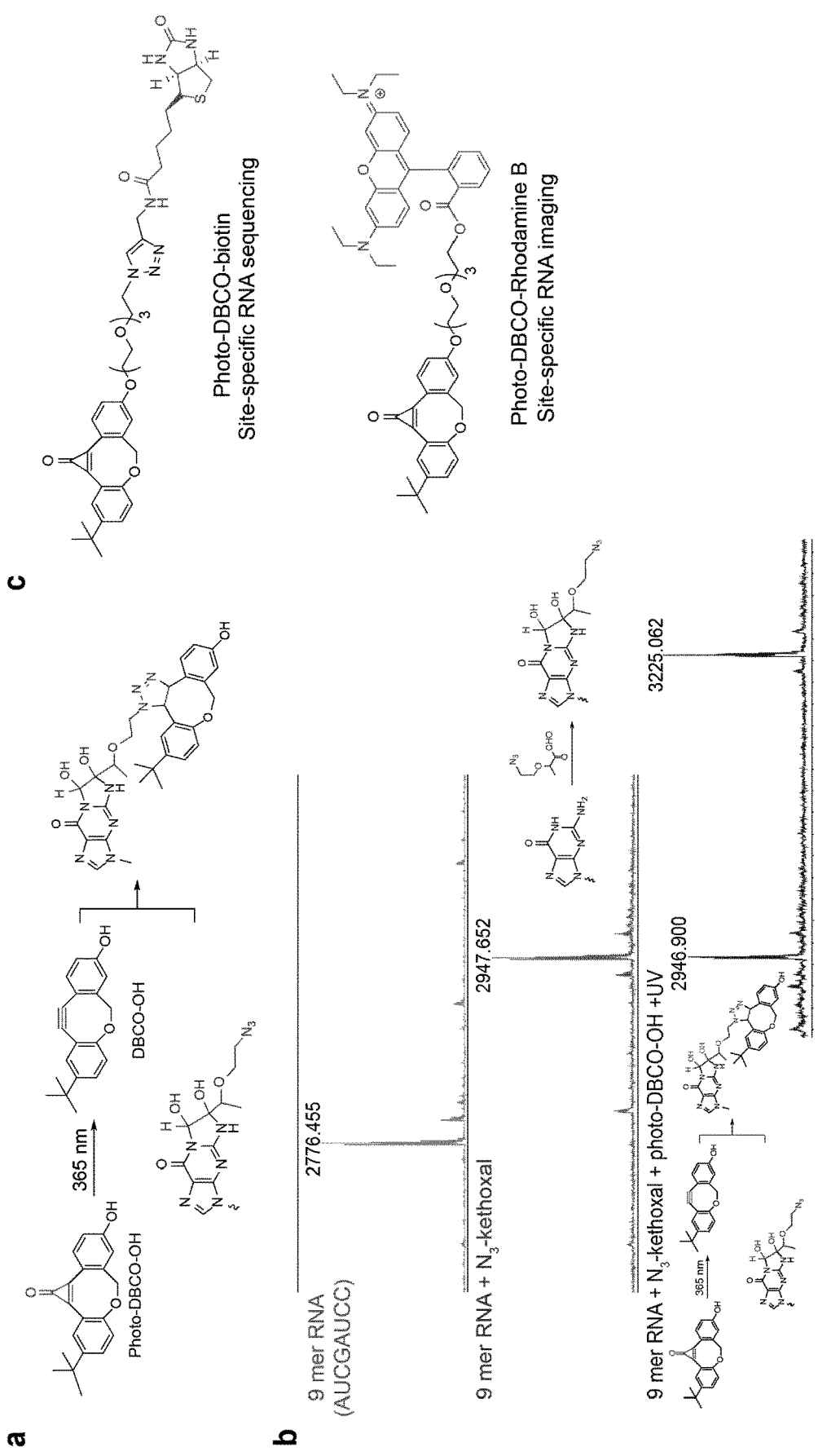
FIG. 6A-C: (a) The scheme of photo-assisted RNA labeling. 365 nm UV triggers the photo-decaging reaction and the product can be captured and conjugated to $N_3$-kethoxal-labelled nucleic acids through "click" chemistry. (b) The mass spectrum analysis of photo-assisted RNA labeling. (c) Two potential functionalization strategies of photo-DBCO-OH and their potential applications in in situ RNA sequencing and imaging.

4. Photoactivated $N_3$-Kethoxal Labeling $N_3$-kethoxal enables in situ nucleic acid labeling by light. Further functionalization of $N_3$-kethoxal labelled DNA/RNA relies on the "click" reaction between DNA/RNAs with azido groups and a DBCO-conjugated molecule. The "click" chemistry can be controlled by light, so as to achieve site-specific DNA/RNA labeling in live cells. As a proof of principle, a caged form of DBCO molecule (photo-DBCO-OH)(Nainar et al., J. Am. Chem. Soc. 139:8090-93, 2017) was involved, which cannot react with the azido group in its native state, but transforms into the activated form (DBCO-OH) and react with $N_3$-kethoxal labelled nucleic acids when exposed to UV light (FIG. 6a). A 9-mer synthetic RNA oligo was incubated with firstly $N_3$-kethoxal, purified, and then incubated with photo-DBCO-OH under 365 nm UV exposure for 10 min. Mass spectrum analysis showed the successful photo-decaging and the following "click" reaction (FIG. 6b). Photo-DBCO-conjugated with biotin or Rhodamine B were synthesized, which can be potentially used for photo-controlled in situ spatial specific RNA sequencing and imaging (FIG. 6c).

5. Protein-RNA Crosslinking Immunoprecipitation Sequencing (CLIP-Seq)

Described herein are methods for pulling down RNAs that bind to a protein of interest, to produce libraries of those RNAs, and to identify regions of the RNAs to which the proteins bind and/or modify. Effective crosslinking of proteins to RNA in the proximity of a protein can be used to perform CLIP-seq to study protein-RNA interactions. The cells are fixed in situ and the kethoxal derivative introduced into the cell, followed by activation of a protein crosslinker. Protein-RNA complexes crosslinked in a cell can then be fragmented, immunoprecipitated, and/or analyzed (FIG. 18).

In some embodiments, the methods include some or all of the following: isolating the complexes; synthesizing DNA complementary to the RNAs to provide an initial population of cDNAs; PCR-amplifying, if necessary, using strand-specific primers; purifying the initial population of cDNAs to obtain a purified population of cDNAs; and high-throughput sequencing the purified population of cDNAs.

In general, to construct dCLIP-seq libraries, RNAs are extracted from a gel using standard techniques. To capture all RNAs (not just polyA RNAs) and to preserve strand information, 3'end-specific adapter can be ligated to the extracted RNA fragments followed by hybridization with reverse transcription primer specific to 3'end adaptor and ligation of second adaptor specific to 5' end. The subsequent reverse transcription step creates first strand cDNA sequence that contains sequences complementary to the 3' and 5' adapters. The resulting PCR using 3'- and 5'-adaptor specific primer pairs is then performed to amplify the cDNAs and the products sequenced via standard methods of high throughput sequencing. Prior to sequencing, a size-selection step can be used in which amplified PCR products of desired sizes are excised after separation by gel electrophoresis in order to remove undesirable side products such as adapter dimers.

Kethoxal derivatives can be modified to include protein crosslinkers, such as diazirine or benzophenone. The current CLIP-seq protocol involves UV-initiated crosslinking of protein amino acid side chains, including aromatic side chains, to RNA bases. These crosslinking reactions suffer from extremely low efficiency. The kethoxal bifunctional molecules described herein are comprised of kethoxal, which allows for efficient RNA labeling, and an efficient protein crosslinker, such as diazirine or benzophenone. Diazarine and benzophenone form radicals upon UV irradiation. The crosslinkers could capture any proximal primary carbon nearby and form a covalent bond thus making it an appropriate reagent for protein crosslinking. Attaching diazirine or benzophenone to a kethoxal derivative enables stabilization of those weak protein interactions. In this way, one can fish the pool of interacting or proximally located RNA to a target protein via pulldown with antibodies specific to the proteins of interest.

Kethoxal derivatives can be prepared that crosslink nucleic acid with protein. In this way, it allows stability of the dynamic nucleic acid-interacting protein complex. After pulldown with specific antibodies, the nucleic acids are then purified and subjected to different library construction or other means of detection. These methods could be served as an improved version of current CLIP with high signal to noise ratio.

Protein cross-linkers include, but are not limited to disuccinimidyl glutarate, disuccinimidyl suberate, disuccinimidyl tartrate, dimethyl adipimidate, dimethyl pimelimidate, dimethyl suberimidate, 1,5-difluoro-2,4-dinitrobenzene, N-maleimidopropionic acid hydrazide, 3-(2-pyridyldithio) propionyl hydrazide, bismaleimidoethane, diazarine, succinimidyl iodoacetate, N-maleimidoacet-oxysuccinimide ester, succinimidyl 3-(2-pyridyldithio)propionate, and benzophenone.

EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Synthesis of Kethoxal Derivatives.

The synthesis route of N$_3$-kethoxal.

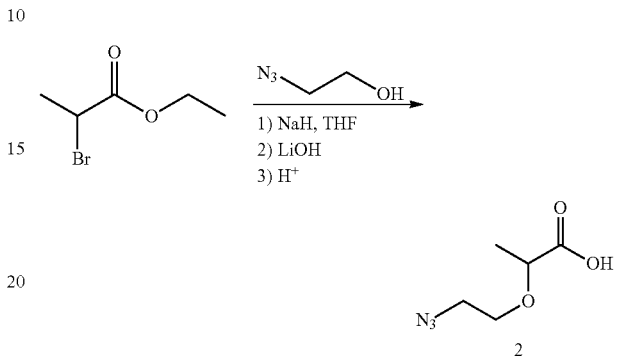

2-(2-azidoethoxy)propanoic acid 2: Sodium hydride (60% dispersion in mineral oil, 6 g, 0.15 mol) was added to a 250 mL two-necked flask, then anhydrous THF 50 mL was added under N$_2$ condition. The suspension was vigorously stirred and cooled to 0° C. 2-Azidoenthanol (8.7 g, 0.1 mol) in 20 mL anhydrous THF was added dropwise over 20 minutes. The solution was stirred at an ambient temperature for 15 mins, then cooled to 0° C. again. Ethyl 2-bromopropionate (27.15 g, 0.15 mol) in 10 mL THF was added dropwise. The reaction mixture was warmed to room temperature and stirred overnight under N$_2$ atmosphere. 100 mL Water was used to quench the reaction and the resulted mixture was washed by diethyl ether three times (3×100 mL). The combined organic layers were dried over anhydrous Na$_2$SO$_4$. The crude product was dissolved in 50 ml THF and was added to LiOH aqueous solution (40 ml, 1 M). The mixture was stirred for 16 h at room temperature. THF was removed and HCl (2 M) was added to pH 2. Then, the THF was extracted by diethyl ether three times (3×100 ml). The combined organic layers were dried over anhydrous NaSO$_4$. After concentration and silica gel chromatography (ethyl acetate:petroleum ether=1:7), the product 2 was collected as colorless oil (6.67 g, 26%). $^1$H NMR (400 MHz, CDCl$_3$): δ=4.09 (q, J=6.9 Hz, 1H), 3.85 (ddd, J=9.8, 5.9, 3.4 Hz, 1H), 3.66-3.58 (m, 1H), 3.55-3.46 (m, 1H), 3.42-3.33 (m, 1H), 1.49 (t, J=9.4 Hz, 3H). $^{13}$C NMR (101 MHz, CDCl$_3$): δ=178.48, 74.98, 69.13, 50.65, 18.47. HRMS C$_3$H$_9$N$_3$O$_3^+$ [M+H]$^+$ calculated 160.07167, found 160.07091.

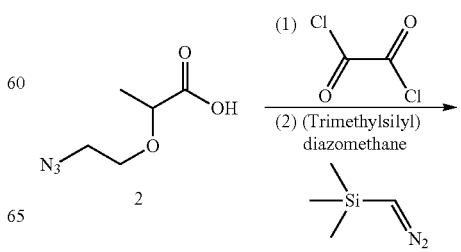

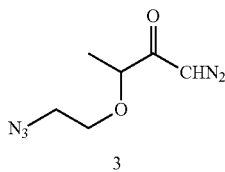

3-(2-azidoethoxy)-1-diazopentane-2-one 3: Under N$_2$ condition, 2 (1.59 g, 10 mmol) was dissolved in 15 mL anhydrous CH$_2$Cl$_2$ and one drop of DMF. Oxalyl chloride (926 µL, 15 mmol) was added to the solution and stirred at room temperature for 2 h. After that, the solvent and excess oxalyl chloride was removed. The residue was dissolved in anhydrous CH$_3$CN 50 mL, cooled to 0° C., and (Trimethylsilyl)diazomethane solution 2 M in diethyl ether (4 mL, 10 mmol) was added dropwise. The reaction mixture was stirred at 0° C. overnight. The solvent was evaporated and silica gel chromatography (ethyl acetate:petroleum ether=1: 7) was performed in order to afford product 3 as yellow oil (620 mg, 33.8%). $^1$H NMR (400 MHz, CDCl$_3$): δ=5.82 (s, 1H), 4.00-3.85 (m, 1H), 3.72-3.60 (m, 2H), 3.48-3.35 (m, 2H), 1.38 (d, J=6.8 Hz, 3H). $^{13}$C NMR (101 MHz, CDCl$_3$): δ=196.94, 80.89, 68.73, 52.30, 50.88, 18.58. HRMS C$_6$H$_9$N$_5$O$_2$$^+$ [M+H]$^+$ calculated 184.0829, found 184.0822.

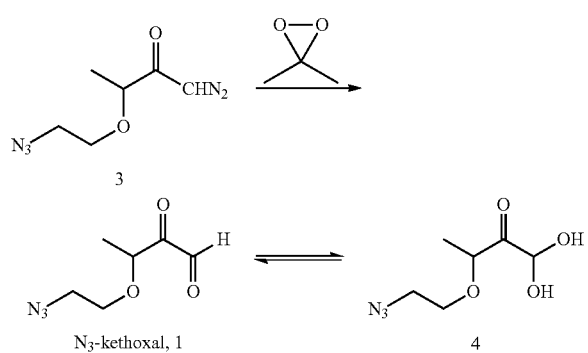

Azido-kethoxal 1 (N$_3$-kethoxal), or 3-(2-azidoethoxy)-1, 1-dihydroxybutan-2-one (4): According to Adam's procedure, the Dimethyldioxirane (DMD) in an acetone solution was prepared. To the compound 3 (183 mg, 1 mmol), 11 mL DMD-acetone was added in several portions. Obvious gas evolution was observed. The reaction mixture was stirred at room temperature until the reaction was complete under TLC monitor to Azido-kethoxal 1 and its hydrate 4 as a yellow oil. $^1$H NMR (400 MHz, CDCl$_3$): δ=[9.5 (m)+5.5 (m), 1H], 4.55-4.40 (m, 1H), 3.75 (m, 2H), 3.50-3.25 (m, 2H), 1.50-1.20 (m, 3H). HRMS C$_6$H$_9$N$_3$O$_3$$^+$ [M+Na]$^+$ calculated 194.0536, found 194.0555.

General chemical and biological materials. All chemical reagents for N$_3$-kethoxal synthesis were purchased from commercial sources. RNA oligoes were purchased from Integrated DNA Technologies, Inc. (IDT) and Takara Biomedical Technology Co., Ltd. Buffer salts and chemical reagents for N$_3$-kethoxal synthesis were purchased from commercial sources. Superscript III, Dynabeads® MyOne™ Streptavidin C1 was purchased from Life technologies. T4 PNK, T4 RNL2tr K227Q, 5'-Deadenylase, RecJ$_f$ were purchased from New England Biolabs. CircLigaseII was purchase from epicenter company. DBCO-Biotin was purchase from Click Chemistry Tools LLC (A116-10). All RNase-free solutions were prepared from DEPC-treated MilliQ-water.

Example 2

Verification of N$_3$-Kethoxal Reaction with Guanine

The N$_3$-kethoxal and guanine reaction was verified. Guanine (100 µM, 2 µL), N$_3$-kethoxal (1 M in DMSO, 1 µL), sodium cacodylate buffer (0.1 M, pH=7.0, 1 µL) and 6 µL ddH$_2$O were added together into 1.5 mL microcentrifuge tube at 37° C. for 10 min. HRMS C$_{11}$H$_{14}$N$_8$O$_4$$^+$ [M+H]$^+$ calculated 323.1216, found 323.1203.

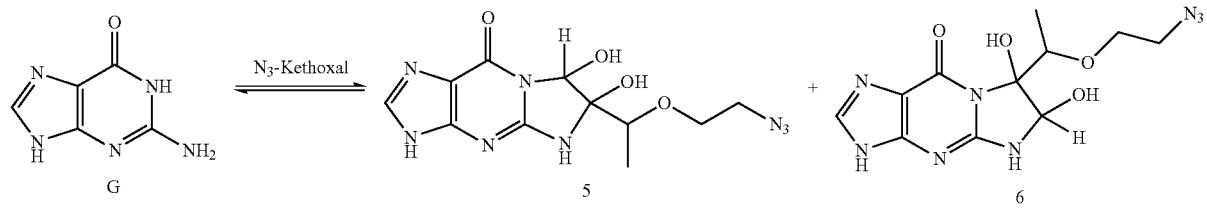 [SMILES: Nc1nc2[nH]cnc2c(=O)[nH]1 ; CC(OCCN=[N+]=[N-])C1(O)Nc2nc3[nH]cnc3c(=O)n2C1O ; CC(OCCN=[N+]=[N-])C1(O)C(O)Nc2nc3[nH]cnc3c(=O)n21]

Example 3

The Reaction of N$_3$-Kethoxal and RNA

The reaction of N$_3$-kethoxal and RNA was generally performed with the following protocol: 100 pmol RNA oligo and 1 µmol N$_3$-kethoxal was incubated in total 10 µL solution in PBS buffer at 37° C. for 10 mins. The modified RNA was purified by Micro Bio-Spin™ P-6 Gel Columns (Biorad, 7326222) to remove residual chemicals. The purified labelled RNA can be used for further studies such as mass spectrometry, gel electrophoresis and copper-free click reaction with biotin-DBCO.

Removal N$_3$-kethoxal modification from N$_3$-kethoxal labelled RNA. The detailed protocol of N$_3$-kethoxal modification erasing is described below "N$_3$-kethoxal-remove sample preparation" in the keth-seq protocol. Generally, the purified N$_3$-kethoxal modified RNA was incubated with high concentration of GTP (½ volume of the reaction solution, final concentration 50 mM) at 37° C. for 6 hours or at 95° C. for 10 mins. Higher temperature benefits the removal the N$_3$-kethoxal modification.

Fixation of N$_3$-kethoxal modification in RNA. The labile N$_3$-kethoxal modification in RNA can be fixed in the presence of borate buffer. The solution of N$_3$-kethoxal labelled RNA was mixed with 1/10 volume of stock borate buffer (final concentration: 50 mM; stock borate buffer: 500 mM potassium borate, pH 7.0, pH was monitored while adding potassium hydroxide pellets to 500 mM boric acid). The borate buffer fixation was used in various steps of keth-seq protocol, see below.

MALDI-TOF-MS analysis of $N_3$-kethoxal labelled RNA oligo. The $N_3$-kethoxal labelled RNA was purified by Micro Bio-Spin™ P-6 Gel Columns. Meanwhile the buffer exchange occurred from PBS buffer to tris buffer that can be directly used in MALDI-TOF-MS experiment without extra desalt step. One microliter of product solution was mixed with one microliter matrix which include 8:1 volume ratio of 2'4'6'-trihydroxyacetophenone (THAP, 10 mg/mL in 50% $CH_3CN/H_2O$):ammonium citrate (50 mg/mL in $H_2O$). Then the mixture was spotted on the MALDI sample plate, dried and analyzed by Bruker Ultraflextreme MALDI-TOF-TOF Mass Spectrometers.

Example 4

The Selectivity of $N_3$-Kethoxal to SSRNA by Gel Electrophoresis.

The complementary RNA oligoes FS1 (5'-FAM-GAGCAGCUUUAGUUUAGAUCGAGUGUA (SEQ ID NO:1, Fluorescent RNA oligo) and S2 (UACACUCGAUC-UAAACUAAAGCUGCUC (SEQ ID NO:2)) were hybridized to double-strand RNA (dsRNA) with the ratio of FS1:S2=1.2:1 to ensure all FS1 was involved in the formation of dsRNA. After the reaction with $N_3$-kethoxal, the purified product by Micro Bio-Spin™ P-6 Gel Columns was analyzed by denaturing gel electrophoresis (Novex™ TBE-Urea Gels, 15%, Invitrogen, EC6885BOX). Gel Imaging was collected in Pharos FX Molecular imager (Bio-Rad, USA).

The product of $N_3$-kethoxal with for RNA nucleic bases was analyzed using LC-6AD (Shimadzu, Japan) HPLC instrument, which equipped with an Inertsil ODS-SP column (5 m, 250×4.6 mm) (GL Science Inc. Japan). The phase A (100 mM TEAA buffer, pH=7.0) and phase B ($CH_3CN$) were used as eluents with a flow rate of 1 mL/min at 35° C. (B conc.: 5-5-30%/0-5-30 min).

Example 5

Biotinylation of $N_3$-Kethoxal Labelled RNA

In vitro study: The purified $N_3$-kethoxal RNA was incubated with DBCO-Biotin at 37° C. for 2 hours in present of RNase inhibitor, borate buffer (see biotinylation of keth-seq protocol below). For RNA oligo, the biotinylated product was purified by Micro Bio-Spin™ P-6 Gel Columns and subject to dot blot assay and MALDI-TOF-MS detection; for total RNA or mRNA, the product was purified by RNA clean & concentrator 5 (zymo research, R1015).

In vivo study: 10 µL $N_3$-kethoxal was added into the cell culture medium in 100 mm cell culture dish with nearly 80% confluent mES cells. After incubation at 37° C. in $CO_2$ incubator for a specific time, the medium was aspirated and the cells were washed three times by PBS. The total RNA was isolated by Trizol™ reagent (Invitrogen, 15596026) or Qiagen RNeasy™ plus mini kit (Qiagen, 74134). mRNA was isolated by Dynabeads™ mRNA DIRECT™ Purification Kit (Invitrogen, 61011). The biotinylation step was same as in vitro study. The biotinylated RNA was purified by RNA clean & concentrator.

Dot blot assay: one microliter RNA (100 ng/uL) sample was spotted onto the Amersham Hybond-N+ membrane (RPN119B, GE Healthcare) and UV crosslinked to the membrane by UVP HL-2000 hybriLinker. The membrane was washed using 1×PBST (0.1% tween-20) and blocked with 5% nonfat dry milk in 1×PBST overnight at 4° C. After four times wash using 1×PBST with ten-minute interval, the streptavidin-horseradish peroxidase (1:15000 dilution, streptavidin-HRP, Life Technologies, S-911) in 1×PBST with 3% BSA was added and incubated at room temperature for 40 mins. Then then membrane was washed using 1×PBST with ten-minute interval again and developed by SuperSignal™ West Pico PLUS Chemiluminescent Substrate (Thermo Scientific, 34577). The membrane was washed by 1×PBST again and stained by methylene blue solution (0.02% methylene blue in 0.3 M sodium Acetate pH 5.2).

Example 6

Keth-Seq Library Preparation

A library was prepared following icSHAPE protocol with slight changes (Spitale et al., Nature 519:486-90, 2015). The detailed protocol is described below. For in vitro library preparation, RNA was isolated and refolded in RNA folding mix buffer firstly (100 mM HEPES, pH 8.0, 100 mM NaCl, 10 mM $MgCl_2$). The refolded RNA was treated with $N_3$-kethoxal and then utilized for library construction. For in vivo study, $N_3$-kethoxal was added into the cultural medium of mES cell and the RNA was isolated to be utilized for library construction.

Sequencing data processing. As the library structure is similar to icSHAPE technique, a similar strategy was used to preprocess the sequencing reads. Pipeline from icSHAPE protocol was used to conduct the data analysis, all the scripts can be accessed at URL github.com/qczhang/icSHAPE. Firstly, script readCollapse.pl was used to collapse the reads with default parameter. Then trimming.pl was used to cut potential adapter sequences (-l 13 -t 0 -c phred33 -a adapter.fa -m 0, adapter sequence: ATGGAATTCTCGGGTGC-CAAGGAACTCCAGTCACATCAC-GATCTCGTATGCCGTC TTCTGCTTGAAAAAAAAAA (SEQ ID NO:3). Next, the clean reads were mapped to ribosomal RNAs, and the unmapped reads were mapped to whole transcriptome (Gencode, mm10 for mouse and hg38 for human) using Bowtie with default parameters. Reverse transcription (RT) stop signal was calculated using script calcRT.pl. After evaluate correlation between different replicates (correlationRT.pl), RT signal of replicates were combined (combineRTreplicates.pl) for subsequent analysis. For both kethoxal and control sample individually, the RT signal are normalized (normalizeRTfile.pl -m mean:vigintile2 -d 32-l 32). Enriched reactivity for each transcript was calculated by comparing kethoxal sample (foreground) versus control sample (background) using script calcEnrich.pl (-w factor5:scaling1 -x 0.25). Finally, specific criteria were used to retain more confident signal (filterEnrich.pl -T 2 -t 200 -s 5 -e 30).

$N_3$-Kethoxal and $N_3$-Kethoxal-Removed Library Preparation.

$N_3$-Kethoxal in vivo labeling. Passage mES cell at the previous day in 10 cm plate with 50% confluency. The second day morning, nearly ~80% confluency. Remove 5 mL medium, then add the 10 µL of $N_3$-kethoxal. Incubate at 37° C. for various minutes. Aspirate medium, use PBS wash twice, add 1 mL PBS, scrape the cell into a 1.5 mL tube. Spin down at 2000 rpm for 5 min at 4° C. Aspirate the supernatant. Use Qiagen RNeasy plus mini kit to isolate total RNA, then use Dynabeads® mRNA Purification Kit to isolate mRNA from total RNA samples.

Biotinylation. (a) Take nearly 2 µg total RNA or mRNA, add 20 mM WS DBCO-Biotin (Click Chemistry tool, A116) in 1.5 mL tube, water bath 37° C. for 2 h. 10×PBS (10 µL), 500 mM borate buffer (5 µL), 20 mM WS DBCO-Biotin (5 µL), SUPERase In RNase Inhibitor (2 µL), RNA solution+

H₂O (78 µL). Total reaction to 100 µL and incubate at 37° C. for 2 h. (borate buffer: 500 mM potassium borate (pH 7.0), pH with potassium hydroxide pellets to 500 mM boric acid) (b) RNA recovery for 100 µL RNA reaction solution. Qiagen RNeasy MinElute Kit. Add 350 µL buffer RLT to 100 µL reaction solution, then add 900 µL 100% Ethanol to mixture. Load solution to Qiagen MinElute column, two 500 µL RPE washes, one no-buffer spin to dry the column. Two 50 µL RNase-free water elute the RNA solution. (Optional) Use dot blot to check the efficiency of biotinylation.

Fragmentation (Sonication). (a) Transfer RNA solution to Bioruptor NGS 0.65 mL Microtubes. Sonicate 30 cycles with 30 s ON/30 s OFF. (b) Lyophilize to 3 µL and perform Ligation.

T4 PNK RNA end repair, 3'-End Ligation and 3'-adaptor remove. (a) T4 PNK End repair (PCR tube, thermo cycle): RNA Sample (3 µL), 10×T4 PNK buffer (1 µL), SUPERase In RNase Inhibitor (1 µL), Borate buffer (1 µL), 10 mM ATP (1 µL), T4 PNK enzyme (2 µL), and FastAP (1 µL). Total 10 µL, incubate at 37° C. for 1 h, and perform 3'-end ligation directly.

(b) 3'-end ligation: RNA solution after T4 PNK repair (10 µL), 3'-Adaptor 20 µM (1 µL), 10×T4RNL2tr buffer (1 µL), 100 mM DTT (1 µL), 50% PEG8000 (6 µL), and T4 RNL2tr K227Q (1.5 µL). Total 20.5 µL, incubate at 16° C. overnight.

(c) Add 29.5 µL H₂O to each sample and purify RNA with Zymo RNA clean & concentrator 5 kit. Elute by 7 µL H₂O twice and get ~13 µL RNA solution. (i) Add 100 µL RNA binding buffer to the 50 µL reaction solution, then add 150 µL 100% Ethanol to mixture. (ii) Load solution to column, 400 µL RNA prep buffer, 700 µL RNA wash buffer, then one no-buffer spin to dry the column. (iii) Two 7 µL RNase-free water elute the RNA solution.

(d) Excess 3'-Adaptor remove: RNA solution (13 µL), NEB buffer 2 (2 µL), 5'-Deadenylase (2 µL), and Borate buffer (1 µL). Total 18 µL, incubate at 30° C. for 30 mins. Then, add RecJ$_f$ 2 µL, total 20 µL, incubate at 37° C. for 1 h. Add 30 µL H₂O to each sample and purify RNA with Zymo RNA clean & concentrator 5 kit. Elute by 7 and 6 µL H₂O twice and get ~12 µL RNA solution.

(e) Separate RNA solution to two fractions. (1) Keep 10.5 µL for N₃-kethoxal sample and move cDNA synthesis step directly. (2) Residual 1.5 µL for N₃-kethoxal-remove sample preparation in N3-kethoxal-remove sample step.

N₃-kethoxal-remove sample preparation: Add GTP solution to remove N₃-kethoxal modification and produce N₃-kethoxal-remove sample. RNA solution (1.5 µL), SUPERase In RNase Inhibitor (1 µL), 100 mM dGTP (5 µL), and H₂O (2.5 µL). Incubate at 95° C. for 10 mins. Then, add 40 µL H₂O to recover RNA by Zymo RNA clean & concentrator 5 kit. Elute twice with 6 µL H₂O then move to cDNA synthesis step. (i) Add 100 µL RNA binding buffer to 50 µL reaction solution, then add 150 µL 100% Ethanol to mixture, mix. (ii) Load solution to column, 400 µL RNA prep buffer, 700 µL RNA wash buffer, one no-buffer spin to dry column. (iii)Two 6 µL RNase-free water elute the RNA solution.

cDNA synthesis. (a) Transfer RNA samples to PCR tube. Add 1 µL 5 µM RT primer, mix. N₃-kethoxal-remove: RNA solution (10.5 µL), 5 µM RT primer (1 µL), and H₂O (1 µL). N₃-kethoxal: RNA solution (10.5 µL), 5 µM RT primer (1 µL), and borate buffer (1 µL). Total 12.5 µL mixture was heated at 70° C. for 5 min in thermocycle, and then cool slowly to 25° C. (1° C. per 1 s, 45 steps) and hold at 25° C. for 1 min.

(b) After primer annealing, the following was added: 5× First Strand Buffer (4 µL), SUPERase In RNase Inhibitor (0.5 µL), 100 mM DTT (1 µL), dNTP 10 mM each (1 µL), and SuperScript III (1 µL). Total 20 µL mixture was incubate at 25° C. for 3 mins, 7 mins at 42° C., and finally at 52° C. for 30 mins, hold at 4° C. After cDNA extension, put the mixture on ice or 4° C., do not raise samples above 37° C. to avoid denaturing conditions.

Streptavidin capture, cDNA elution (Strepavidin capture ONLY for N₃-kethoxal sample, NOT for N₃-kethoxal-remove sample). Biotin Binding Buffer: 100 mM Tris-HCl pH 7.0, 10 mM EDTA, 1 M NaCl. Biotin Wash Buffer: 10 mM Tris-HCl pH 7.0, 1 mM EDTA, 4 M NaCl, 0.2% Tween. 10× RNaseH buffer: 500 mM HEPES, 750 mM NaCl, 30 mM MgCl₂, 1.25% Sarkosyl, 0.25% Nadeoxycholate, 50 mM DTT.

(a) Per sample, 20 µL Dynabeads® MyOne™ Streptavidin C1 was washed twice with 1 mL Biotin Binding buffer. After wash, resuspend the beads in 10 µL beads binding buffer and 1 µL SUPERase In RNase Inhibitor. Then store on ice until needed. (b) 10 µL of pre-washed beads are added to each Reverse Transcription kethoxal sample (20 µL), and incubated at room temperature for 45 mins with rotation. (c) After streptavidin capture, add 100 µL Biotin Wash Buffer and transfer to 1.5 mL tubes. Add additional 400 µL Biotin Wash Buffer (total 500 µL) and invert the tubes four times to mix. (d) Apply the samples to magnet rack. Remove the supernatant. Then, use 500 µL Biotin Wash Buffer to wash four more time. (Total 5 washes). (e) Wash the samples twice using 500 µL 1×PBS. (f) cDNA elution (for Kethoxal sample): (i) cDNA is eluted by adding following solution: 10× RNaseH buffer (5 µL), RNaseA/T1 cocktail (1 µL), RNaseH (1 µL), 50 mM D-biotin (12.5 µL), and H₂O (30.5 µL). Total 50 µL solution was incubated at 37° C. for 30 mins in Thermomixer at 1000 r.p.m. (ii) Samples are mixed with 1 µL 100% DMSO, heated to 95° C. for 4 mins, placed on a magnet rack, and transfer the 50 µL cDNA elution to a new tube. (g) Purify cDNA using DNA Clean & Concentrator-5 Kit with modified method: 50 µL cDNA elution solution, add 350 µl of DNA Binding Buffer and 350 µl of 100% ethanol. Mix well. Continue with purification according to the manufacturer's instructions (200 µL wash buffer wash twice, then empty spin once). Elute cDNA twice with 10 µL H₂O. Get total ~20 µL cDNA solution. Lyophilize to ~5 µL solution.

cDNA elution (ONLY for N₃-kethoxal-remove sample, NOT for N₃-kethoxal sample). (a) cDNA of N₃-kethoxal-remove sample is eluted by adding following solution to 20 µL RT reaction solution: 10× RNaseH buffer (5 µL), RNaseA/T1 cocktail (2 µL), RNaseH (2 µL), and H₂O (21 µL). Total 50 µL solution was incubated at 37° C. for 30 mins. (b) Purify cDNA using DNA Clean & Concentrator-5 Kit with modified method: 50 µL cDNA elution solution, add 350 µl of DNA Binding Buffer and 350 µl of 100% ethanol. Mix well. Continue with purification according to the manufacturer's instructions (200 µL wash buffer wash twice, then empty spin once). Elute cDNA twice with 10 µL H₂O. Get total ~20 µL cDNA solution. Lyophilize to ~5 µL solution.

cDNA size selection. Add 5 µL TBU 2× loading dye, and load to 6% TBE-Urea gel for size selection as well as heating samples to 95° C. for 2 mins, inserting in ice immediately before PAGE separation (180 V, 40 mins). Sybr Gold staining, image and cut >70 nucleotide (70~500) in the gel. Purify the cDNA from the gel. Transfer each gel slice to a 0.5 ml microcentrifuge tube with a hole punched in the bottom using a sterile needle, and close the tube cap. Place each 0.5 ml tube inside a 1.5 ml tube and centrifuge for 2 minutes at ~12,000×g in a microcentrifuge to shred the gel slices. Remove and discard the 0.5 ml tubes. To each 1.5 ml collection tube, add: Nuclease-Free Water (400 µL), 5 M ammonium acetate (40 µL), and 10% SDS (2 µL). Gently rock the samples at 50° C. more than 3 hours to elute the cDNA from the disrupted gel slices. Transfer the slurry to new 1.5 ml filter tubes and centrifuge for ~2 min at maxi-speed to separate the disrupted gel pieces from the eluted cDNA solution. To each aqueous solution, add 2 µl of Glycogen and 700 µl of 100% isopropanol. Store at −80° C. for >1 hour. Centrifuge the tubes at 4° C. for 30 minutes at >12,000 g to pellet the cDNA. Wash the pellet with ice-cold 80% ethanol and air-dry. Resuspend the pellet in 14 µl of Nuclease-Free Water.

cDNA cyclization. (a) Transfer 14 µL cDNA solution to PCR tube, then add reagents as follows: cDNA/$H_2O$ (14 µL), 10× CircLigaseII buffer (2 µL), 1 mM ATP (1 µL), 50 mM $MnCl_2$ (1 µL), and CircLigase I (2 µL). Total 20 µL is incubated at 60° C. for 2 h. (b) Purify the CircDNA using DNA Clean & Concentrator-5 Kit with modified method: Add 30 µL $H_2O$ to the cDNA solution to get 50 µL solution, then add 350 µl of DNA Binding Buffer and 350 µl of 100% ethanol. Mix well. Continue with purification according to the manufacturer's instructions (200 µL wash buffer wash twice, then empty spin once). Elute cDNA twice with 10 µL $H_2O$. Get total ~20 µL CircDNA solution.

Library PCR. (a) Using 1 µL CircDNA for qPCR monitoring to optimize the PCR cycle numbers. RP/RPI short primer 20mer 5 µM (1 µL), CircDNA from cDNA cyclization step (1 µL), $H_2O$ (8 µL), and qPCR 2× Master mix (10 µL). A suggested cycle number is one located at half of the sigmoid curve. (b) PCR by short primer (RP/RPI short 20 mer). Phusion MM (25 µL), RP/RPI short primer 20mer 5 µM (1 µL), CircDNA solution (5 µL), and $H_2O$ (19 µL). Total 50 µL, PCR parameter: 98° C. 30 s, then 98° C. 10 s/60° C. 30 s/72° C. 30 s each cycle. (c) Purify PCR products using Bio-rad Green spin column. Lyophilize to 5 µL, add 2 µL DNA 6× loading dye, and load to 6% TBE gel for size selection (180 V, 30 mins). Sybr-Gold staining, image and cut >80 nucleotide (80~300) in the gel. Purify the cDNA as the protocol in step 8. Resuspend the pellet in 20 µl of Nuclease-Free Water. (d) PCR by Sequencing primer (RP/RPI index X, 3~5 cycle). Phusion MM (25 µL), RP primer 10 µM (1 µL), RPI index x 10 µM (1 µL), Purified DNA (20 µL), and $H_2O$ (3 µL). Total 50 µL, PCR parameter: 98° C. 30 s, then 98° C. 10 s/60° C. 30 s/72° C. 30 s, 3-5 cycles. (e) After sequencing PCR, using 3% Low melting Agarose gel to purify the PCR products (remove primer dimer, 90 V, 45 mins) and recovery by Qiagen QIAquick gel extraction Kit. Elute DNA library by 20 µL $H_2O$.

Example 7

Experiment Procedure for Single-Stranded DNA (ssDNA) Mapping ssDNA is performed by: (1) Prepare labeling medium by adding 5 µL pure $N_3$-kethoxal to 5 mL pre-warmed cell culture medium for each 10 cm dish. (2) Incubate cells in the labeling medium for 10 min at 37° C., 5% $CO_2$. (3) For transcription inhibition experiments, cells were treated for 2 h under 100 µM DRB or 1 µM triptolide before incubated in N3-kethoxal-containing medium. (4) Harvest cells after the 10 min incubation, isolate total DNA from cells by PureLink genomic DNA mini kit according to the manufacturer's protocol. (5) Suspend 5 µg total DNA in 85 µL $H_2O$, then add 10 µL 10×PBS and 5 µL 20 mM DBCO-PEG4-biotin (DMSO solution), incubate the mixture at 37° C. for 2 h. (6) Add 5 µL RNase A to the reaction mixture, incubate the mixture at 37° C. for another 15 min. (7) Recover DNA from the reaction mixture by DNA Clean & Concentrator kit according to the manufacturer's protocol.

Libraries were constructed by different commercial library construction kits with similar results obtained. Two examples include:

(8a) The use of Accel-NGS Methyl-seq DNA library kit (Swift): (i) Fragment 2 µg of recovered DNA from step 7 by sonication under 30 s-on/30 s-off setting for 30 cycles. (ii) Save 5% of the fragmented DNA for input, use the rest 95% to enrich biotin-tagged DNA by 10 µL pre-washed Streptavidin C1 beads according to the manufacturer's protocol with minor changes. Beads were washed 3 times in 1× binding and wash buffer with 0.05% tween-20 before re-suspended in 95 µL 2× binding and wash buffer with 0.1% tween-20. Beads were mixed with DNA and the mixture was incubated at room temperature for 15 min with gentle rotation. After incubation, beads were washed 5 times with 1× binding and wash buffer with 0.05% tween-20. (iii) Elute the enriched DNA by heating the beads in 30 µL H2O at 95° C. for 10 min. Treat the saved input at 95° C. for 10 min at the same time. The put both input and IP samples on ice immediately. (iv) Proceed to library construction according the protocol from the Accel-NGS Methyl-seq DNA library kit.

(8b) The use of Kapa Hyper Plus kit (Kapa Biosystems): (i) Suspend 1 µg total DNA in 35 µL $H_2O$, add 5 µL Kapa fragmentation buffer and 10 µL Kapa fragmentation enzyme. Incubate the mixture at 37° C. for 30 min. (ii) Recovery fragmented DNA by DNA Clean & Concentrator kit according to the manufacturer's protocol. (iii) Perform A-tailing and adapter ligation according the protocol from Kapa Hyper Plus kit. (iv) Save 5% of the DNA for input, use the rest 95% to enrich biotin-tagged DNA by 10 µL pre-washed Streptavidin C1 beads according to the manufacturer's protocol with minor changes. Beads were washed 3 times in 1× binding and wash buffer with 0.05% tween-20, before re-suspended in 95 µL 2× binding and wash buffer with 0.1% tween-20. Beads were mixed with DNA and the mixture was incubated at room temperature for 15 min with gentle rotate. After incubation, beads were washed 5 times with 1× binding and wash buffer with 0.05% tween-20. (v) Elute the enriched DNA by heating the beads in 25 µL $H_2O$ at 95° C. for 10 min. (vi) PCR amplify the libraries for both input and IP samples according to the protocol from Kapa Hyper Plus kit. (9) Sequence libraries on Nextseq SR80 mode and perform downstream analysis.

Example 8

Experiment Procedure for Kethoxal-Assisted RNA-RNA Interaction (KARRI)

KARRI is performed by: (1) Suspend live cells in 1% formaldehyde solution at $1×10^6$/mL and incubate at room temperature for 10 min with gentle rotate. Then quench this reaction by adding glycine to a final concentration of 125 mM and rotate the mixture at room temperature for 5 min. For translation inhibitor treatment, cells were treated with 100 µg/mL cycloheximide or 3 µg/mL harringtonine at 37° C. for 10 min. (2) Collect and take $2×10^6$ cells. Dilute $N_3$-Kethoxal by 1:5 using DMSO. Make a labeling buffer by adding 10 µL $N_3$-Kethoxal into 290 µL lysis buffer (10 mM Tris-HCl pH 8.0, 10 mM NaCl, 0.2 IGEPAL CA630) with 3 µL 100× proteinase inhibitor cocktail. (3) Suspend cells in labeling buffer and rotate at room temperature for 30 min, then centrifuge at 2500 g for 5 min at 4° C. to collect cells. (4) Wash cell pellets with 500 µL ice-cold lysis buffer for 3 times. (5) Suspend the pellet in 500 µL MeOH containing 10

μM dendrimers, rotate for 1 h at 37° C. Then centrifuge at 2500 g for 5 min at 4° C. to collect cells. (6) Wash cell pellet twice with 500 μL ice-cold lysis buffer. (7) Resuspend cells in 385 μL lysis buffer, add 50 μL 10% SDS, 30 μL proteinase K, 10 μL RNase inhibitor, 25 μL 500 mM $K_3BO_3$, shake at 65° C. for 2 h. (8) Add 500 μL phenol-chloroform to extract RNA and purify RNA by EtOH precipitation. (9) Suspend RNA pellets in 104 μL $H_2O$, add 12 μL 10× DNase I buffer (100 mM Tris-HCl pH 7.4, 25 mM $MgCl_2$, 1 mM $CaCl_2$)), 2 μL DNase I (Thermo), 2 μL RNase inhibitor, and incubate at 37° C. for 30 min with gentle shaking. (10) Add 130 μL 2× proteinase K buffer (100 mM Tris-HCl pH 7.5, 200 mM NaCl, 2 mM EDTA, 1% SDS), 10 μL proteinase K to the reaction, incubate at 65° C. for 30 min with shaking. (11) Extract RNA with 300 μL phenol-chloroform and purify RNA by EtOH precipitation. (12) Suspend RNA pellets in 61 μL $H_2O$, add 7 μL 10× fragmentation buffer (Thermo), 2 μL RNase inhibitor, incubate at 70° C. for 15 min, then add 8 μL fragmentation stop buffer (Thermo) and put the sample on ice immediately to quench the reaction. (13) Enrich crosslinked RNA by using 30 μL pre-washed Streptavidin C1 beads according to the manufacturer's protocol with minor changes. Beads were washed 3 times in 1× binding and wash buffer with 0.05% tween-20, before re-suspended in 80 μL 2× binding and wash buffer with 0.1% tween-20. Beads were mixed with DNA and the mixture was incubated at room temperature for 30 min with gentle rotate. After incubation, beads were washed 3 times with 1× binding and wash buffer with 0.05% tween-20 and once with 1×PNK buffer (NEB). (14) Suspend beads in 41 μL $H_2O$, 5 μL 10×PNK buffer (NEB), 3 μL T4 PNK (NEB), 1 μL RNase inhibitor and shake at 37° C. for 30 min, then add another 3 μL T4 PNK and 6 μL 10 mM ATP, shake at 37° C. for another 30 min. (15) Wash beads twice with 1× binding and wash buffer with 0.05% tween-20, once with 1× ligation buffer (NEB). (16) Suspend beads in 668 μL $H_2O$, 100 μL 10× ligase buffer (NEB), 10 μL RNase inhibitor, 2 μL 10 mM ATP, 20 μL T4 RNA ligase 2 (high concentration) (NEB), 200 μL 50% PEG 8000, rotate at 16° C. for 16 h. (17) Wash beads twice with 1× binding and wash buffer with 0.05% tween-20, once with $H_2O$. Then elute RNA by heating the beads in 30 μL $H_2O$ and shaking beads at 95° C. for 10 min. (18) Take half of the recovered RNA for library construction using the SMARTer Stranded Total RNA-seq Kit v2—Pico Input (Takara) by following the protocol from the manufacturer. (19) Sequence libraries on Novaseq PE150 mode and perform downstream analysis.

The invention claimed is:
1. A compound of the formula:

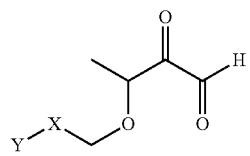

Formula IIa wherein Y is an alkyne, an azide, a strained alkyne, a diene, a dieneophile, an alkoxyamine, a phosphine, a hydrazide, a thiol, or an alkene; and
X is a C1 to C10 alkyl or a C4 to C10 polyethylene glycol linker.

2. The compound of claim 1, wherein Y is an azide.

3. A compound of the formula:

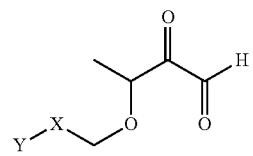

Formula II wherein Y is an alkyne, an azide, a strained alkyne, a diene, a dieneophile, an alkoxyamine, a phosphine, a hydrazide, a thiol, or an alkene; and X is $CH_2$.

4. The compound of claim 1, wherein the compound is of formula:

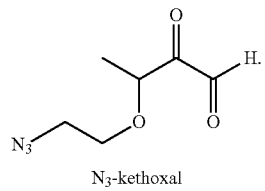

N3-kethoxal

5. A method for labeling a guanine base comprising contacting a guanine base to be labeled with a compound of claim 1 to form a reaction mixture and incubating the reaction mixture at 30 to 40° C. for at least 5 minutes.

6. The method of claim 5, wherein the compound is N3-kethoxal.

7. The method of claim 5, wherein the guanine base is comprised in a polynucleotide.

8. The method of claim 5, wherein the polynucleotide is a ribonucleic acid (RNA).

9. The method of claim 5, wherein the polynucleotide is a deoxyribonucleic acid (DNA).

10. A method for labeling a single stranded nucleic acid in a cell comprising
(i) contacting a target cell with a compound of claim 1, wherein Y is an azide, to form a treated cell comprising a nucleic acid having kethoxal derivative-labeled guanine bases;
(ii) contacting the treated cell with a crosslinking moiety comprising at least two click chemistry reactive moieties and a tag, wherein the crosslinking moiety crosslinks two proximal kethoxal derivative-labeled guanines to form a crosslinked nucleic acid; and
(iii) fragmenting and isolating the crosslinked nucleic acid using a reagent with an affinity for the tag;
wherein the click chemistry reactive moieties are alkyne moieties.

11. The method of claim 10, wherein the tag is biotin, and wherein the reagent with an affinity for the tag is streptavidin.

12. The method of claim 10, wherein the click chemistry reactive moieties are dibenzocyclooctyne moieties.

13. The method of claim 10, wherein the crosslinked nucleic acid is RNA.

14. A compound having the formula:
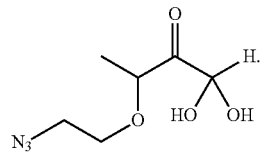
Formula 4
15. A composition comprising the compound of claim 14.
\* \* \* \* \*